United States Patent
Swarts

(10) Patent No.: US 11,890,041 B2
(45) Date of Patent: Feb. 6, 2024

(54) FLEXIBLE CONSTRUCT FOR FEMORAL RECONSTRUCTION

(71) Applicant: Howmedica Osteonics Corp., Mahwah, NJ (US)

(72) Inventor: Dale Frederick Swarts, Warsaw, IN (US)

(73) Assignee: Howmedica Osteonics Corp., Mahwah, NJ (US)

( * ) Notice: Subject to any disclaimer, the term of this patent is extended or adjusted under 35 U.S.C. 154(b) by 443 days.

(21) Appl. No.: 17/116,544

(22) Filed: Dec. 9, 2020

(65) Prior Publication Data
US 2021/0100597 A1    Apr. 8, 2021

Related U.S. Application Data

(63) Continuation of application No. 16/177,775, filed on Nov. 1, 2018, now Pat. No. 10,888,362.

(60) Provisional application No. 62/581,259, filed on Nov. 3, 2017.

(51) Int. Cl.
*A61B 17/80* (2006.01)
*A61B 17/82* (2006.01)
*A61F 2/28* (2006.01)

(52) U.S. Cl.
CPC ...... *A61B 17/8085* (2013.01); *A61B 17/8061* (2013.01); *A61B 17/82* (2013.01); *A61B 17/826* (2013.01); *A61F 2/28* (2013.01)

(58) Field of Classification Search
CPC ............................ A61B 17/8085; A61B 17/82
See application file for complete search history.

(56) References Cited

U.S. PATENT DOCUMENTS

| | | | |
|---|---|---|---|
| 4,064,567 A | 12/1977 | Burstein et al. | |
| 4,089,071 A | 5/1978 | Kalnberz et al. | |
| 4,479,271 A | 10/1984 | Bolesky et al. | |
| 4,570,271 A | 2/1986 | Sump | |
| 4,608,052 A | 8/1986 | Van Kampen et al. | |

(Continued)

FOREIGN PATENT DOCUMENTS

| | | |
|---|---|---|
| DE | 2842847 A1 | 4/1980 |
| DE | 202004018209 U1 | 1/2005 |

(Continued)

OTHER PUBLICATIONS

Wang et al: "A Unit Cell Approach for Lightweight Structure and Compliant Mechanism", Dissertation, Dec. 1, 2005 (Dec. 1, 2005), XP055671658, Retrieved from the Internet:URL:https://pdfs.semanticscholar.org/f827/90e48d743feb2faf1d5da2a960cf1d9611c2.pdf [retrieved on Feb. 26, 2020].

(Continued)

*Primary Examiner* — Andrew Yang
(74) *Attorney, Agent, or Firm* — Lerner David LLP

(57) ABSTRACT

A bone repair device includes a plate having a pathway and a flexible structure. The plate includes opposing top and bottom surfaces and a first side extending between the top and the bottom surfaces. The flexible structure is directly attached to and extends from the first side of the plate. In operation, the bone repair device is placed around and over a plurality of bone parts. The plate is secured to the plurality of bone parts with a cable inserted through the pathway and wrapped around the bone parts.

20 Claims, 19 Drawing Sheets

(56) References Cited

U.S. PATENT DOCUMENTS

| | | |
|---|---|---|
| 4,636,219 A | 1/1987 | Pratt et al. |
| 4,693,721 A | 9/1987 | Ducheyne |
| 4,715,860 A | 12/1987 | Amstutz et al. |
| 4,769,041 A | 9/1988 | Morscher |
| 4,829,152 A | 5/1989 | Rostoker et al. |
| 4,863,474 A | 9/1989 | Brown et al. |
| 4,863,538 A | 9/1989 | Deckard |
| 4,944,817 A | 7/1990 | Bourell et al. |
| 4,969,904 A | 11/1990 | Koch et al. |
| 4,976,738 A | 12/1990 | Frey et al. |
| 4,990,163 A | 2/1991 | Ducheyne et al. |
| 4,997,445 A | 3/1991 | Hodorek |
| 5,013,324 A | 5/1991 | Zolman et al. |
| 5,017,753 A | 5/1991 | Deckard |
| 5,030,233 A | 7/1991 | Ducheyne |
| 5,076,869 A | 12/1991 | Bourell et al. |
| 5,076,875 A | 12/1991 | Padden |
| 5,108,435 A | 4/1992 | Gustavson et al. |
| 5,156,625 A | 10/1992 | Marchetti et al. |
| 5,234,457 A | 8/1993 | Andersen |
| 5,368,602 A | 11/1994 | de la Torre |
| 5,397,359 A | 3/1995 | Mittelmeier et al. |
| 5,433,750 A | 7/1995 | Gradinger et al. |
| 5,443,510 A | 8/1995 | Shetty et al. |
| 5,510,066 A | 4/1996 | Fink et al. |
| 5,590,454 A | 1/1997 | Richardson |
| 5,597,589 A | 1/1997 | Deckard |
| 5,629,077 A | 5/1997 | Turnlund et al. |
| 5,658,334 A | 8/1997 | Caldarise et al. |
| 5,662,713 A | 9/1997 | Andersen et al. |
| 5,711,960 A | 1/1998 | Shikinami |
| 5,718,159 A | 2/1998 | Thompson |
| 5,734,959 A | 3/1998 | Krebs et al. |
| 5,899,935 A | 5/1999 | Ding |
| 5,926,685 A | 7/1999 | Krebs et al. |
| 5,948,342 A | 9/1999 | Nakazawa et al. |
| 5,968,091 A | 10/1999 | Pinchuk et al. |
| 5,984,926 A | 11/1999 | Jones |
| 6,031,148 A | 2/2000 | Hayes et al. |
| 6,113,640 A | 9/2000 | Tormala et al. |
| 6,132,674 A | 10/2000 | Compton et al. |
| 6,146,416 A | 11/2000 | Andersen et al. |
| 6,204,207 B1 | 3/2001 | Cederblad et al. |
| 6,206,924 B1 | 3/2001 | Timm |
| 6,240,616 B1 | 6/2001 | Yan |
| 6,241,757 B1 | 6/2001 | An et al. |
| 6,249,952 B1 | 6/2001 | Ding |
| 6,312,473 B1 | 11/2001 | Oshida |
| 6,342,068 B1 | 1/2002 | Thompson |
| 6,355,070 B1 | 3/2002 | Andersen et al. |
| 6,379,816 B1 | 4/2002 | De Loose et al. |
| 6,403,241 B1 | 6/2002 | Chen et al. |
| 6,461,385 B1 | 10/2002 | Gayer et al. |
| 6,497,728 B2 | 12/2002 | Yong |
| 6,505,654 B1 | 1/2003 | Andersen et al. |
| 6,524,344 B2 | 2/2003 | Yoon |
| 6,544,472 B1 | 4/2003 | Compton et al. |
| 6,592,617 B2 | 7/2003 | Thompson |
| 6,685,990 B1 | 2/2004 | Zhong et al. |
| 6,692,606 B1 | 2/2004 | Cederblad et al. |
| 6,695,884 B1 | 2/2004 | Townley |
| 6,716,514 B2 | 4/2004 | Nissing |
| 6,723,120 B2 | 4/2004 | Yan |
| 6,746,483 B1 | 6/2004 | Bojarski et al. |
| 6,783,554 B2 | 8/2004 | Amara et al. |
| 6,805,966 B1 | 10/2004 | Formato et al. |
| 6,827,743 B2 | 12/2004 | Eisermann et al. |
| 7,052,513 B2 | 5/2006 | Thompson |
| 7,189,263 B2 | 3/2007 | Erbe et al. |
| 7,252,685 B2 | 8/2007 | Bindseil et al. |
| 7,279,008 B2 | 10/2007 | Brown et al. |
| 7,341,601 B2 | 3/2008 | Eisermann et al. |
| 7,344,560 B2 | 3/2008 | Gregorich et al. |
| 7,407,512 B2 | 8/2008 | Bojarski et al. |
| 7,465,318 B2 | 12/2008 | Sennett et al. |
| 7,527,644 B2 | 5/2009 | Mangiardi et al. |
| 7,531,004 B2 | 5/2009 | Bagga et al. |
| 7,534,451 B2 | 5/2009 | Erbe et al. |
| 7,537,664 B2 | 5/2009 | O'Neill et al. |
| 7,637,942 B2 | 12/2009 | Mangiardi et al. |
| 7,655,047 B2 | 2/2010 | Swords |
| 7,682,400 B2 | 3/2010 | Zwirkoski |
| 7,699,890 B2 | 4/2010 | Yan |
| 7,731,750 B2 | 6/2010 | Bojarski et al. |
| 7,740,657 B2 | 6/2010 | Brown, Jr. et al. |
| 7,749,264 B2 | 7/2010 | Gregorich et al. |
| 7,758,642 B2 | 7/2010 | Bojarski et al. |
| 7,824,433 B2 * | 11/2010 | Williams ........... A61B 17/8085 606/283 |
| 7,828,802 B2 | 11/2010 | Levy et al. |
| 7,931,931 B2 | 4/2011 | Yan |
| 7,964,206 B2 | 6/2011 | Suokas et al. |
| 7,988,732 B2 | 8/2011 | Bojarski et al. |
| 8,007,529 B2 | 8/2011 | Yan |
| 8,029,506 B2 | 10/2011 | Levy et al. |
| 8,052,743 B2 | 11/2011 | Weber et al. |
| 8,100,973 B2 | 1/2012 | Sennett et al. |
| 8,142,886 B2 | 3/2012 | Noble et al. |
| 8,147,861 B2 | 4/2012 | Jones et al. |
| 8,172,897 B2 | 5/2012 | Gale et al. |
| 8,206,436 B2 | 6/2012 | Mangiardi et al. |
| 8,211,168 B2 | 7/2012 | Purdy et al. |
| 8,241,357 B2 | 8/2012 | Bhatnagar et al. |
| 8,247,333 B2 | 8/2012 | Sypeck et al. |
| 8,257,395 B2 | 9/2012 | Bhatnagar et al. |
| 8,268,099 B2 | 9/2012 | O'Neill et al. |
| 8,268,100 B2 | 9/2012 | O'Neill et al. |
| 8,287,915 B2 | 10/2012 | Clineff et al. |
| 8,329,091 B2 | 12/2012 | Maffia |
| 8,350,186 B2 | 1/2013 | Jones et al. |
| 8,382,837 B2 | 2/2013 | Sennett et al. |
| 8,430,930 B2 | 4/2013 | Hunt |
| 8,454,705 B2 | 6/2013 | Pressacco et al. |
| 8,461,478 B2 | 6/2013 | Chen et al. |
| 8,532,806 B1 | 9/2013 | Masson |
| 8,551,173 B2 | 10/2013 | Lechmann et al. |
| 8,556,981 B2 | 10/2013 | Jones et al. |
| 8,679,166 B2 | 3/2014 | Bhatnagar et al. |
| 8,728,387 B2 | 5/2014 | Jones et al. |
| 8,734,520 B2 | 5/2014 | Zwirkoski |
| 8,764,809 B2 * | 7/2014 | Lorenz ................ A61B 17/74 606/283 |
| 8,814,930 B2 | 8/2014 | Zheng et al. |
| 8,831,501 B2 | 9/2014 | Vella et al. |
| 8,888,862 B2 | 11/2014 | McDonnell et al. |
| 8,900,620 B2 | 12/2014 | Fulmer et al. |
| 8,906,022 B2 * | 12/2014 | Krinke ................ A61B 17/68 606/63 |
| 8,932,366 B2 | 1/2015 | Shih |
| 8,956,394 B1 | 2/2015 | McDonnell |
| 8,986,767 B2 | 3/2015 | Batchelder |
| 8,992,537 B1 | 3/2015 | McDonnell |
| 8,992,619 B2 | 3/2015 | Patterson et al. |
| 8,992,703 B2 | 3/2015 | O'Neill et al. |
| 9,052,481 B2 | 6/2015 | Brunner et al. |
| 9,114,032 B1 | 8/2015 | Pulugurtha |
| 9,135,374 B2 | 9/2015 | Jones et al. |
| D740,427 S | 10/2015 | McDonnell et al. |
| 9,155,819 B2 | 10/2015 | Fonte et al. |
| 9,180,010 B2 | 11/2015 | Dong et al. |
| 9,206,827 B2 | 12/2015 | Loree et al. |
| 9,232,971 B2 | 1/2016 | Sennett |
| 9,237,917 B2 | 1/2016 | Sennett et al. |
| 9,254,199 B2 | 2/2016 | Biedermann et al. |
| 9,265,601 B2 | 2/2016 | Bojarski et al. |
| 9,408,651 B2 | 8/2016 | Sennett et al. |
| 9,415,137 B2 | 8/2016 | Meridew et al. |
| 9,421,108 B2 | 8/2016 | Hunt |
| 9,456,901 B2 | 10/2016 | Jones et al. |
| 9,526,539 B2 | 12/2016 | Zwirkoski |
| 9,526,544 B1 | 12/2016 | Kumar |
| 9,527,273 B2 | 12/2016 | Moors |
| 9,532,806 B2 | 1/2017 | McDonnell |
| 9,545,317 B2 | 1/2017 | Hunt |

(56) References Cited

U.S. PATENT DOCUMENTS

| | | | |
|---|---|---|---|
| 9,642,727 B2 | 5/2017 | Verschueren et al. | |
| 9,777,380 B2 | 10/2017 | MacDonald et al. | |
| 9,833,955 B2 | 12/2017 | Muller et al. | |
| 9,907,593 B2 | 3/2018 | McDonnell | |
| 9,918,849 B2 | 3/2018 | Morris et al. | |
| 9,943,351 B2 | 4/2018 | McDonnell et al. | |
| 9,993,277 B2 | 6/2018 | Krinke et al. | |
| 10,016,076 B2 | 7/2018 | Frazier | |
| 10,029,422 B2 | 7/2018 | Meisner et al. | |
| 10,070,975 B2 | 9/2018 | Dugan et al. | |
| 10,092,404 B2 | 10/2018 | Hanssen et al. | |
| 10,433,977 B2 | 10/2019 | Lechmann et al. | |
| 10,499,966 B2 | 12/2019 | Kobayashi et al. | |
| 10,517,658 B2 * | 12/2019 | Cremer | A61B 17/82 |
| 2001/0013116 A1 | 8/2001 | Watanabe et al. | |
| 2003/0109784 A1 | 6/2003 | Loh et al. | |
| 2005/0119758 A1 | 6/2005 | Alexander et al. | |
| 2005/0256582 A1 | 11/2005 | Ferree | |
| 2005/0283229 A1 | 12/2005 | Dugan et al. | |
| 2006/0147332 A1 | 7/2006 | Jones et al. | |
| 2006/0166807 A1 | 7/2006 | Ylanen et al. | |
| 2007/0141111 A1 | 6/2007 | Suokas et al. | |
| 2007/0142914 A1 | 6/2007 | Jones et al. | |
| 2007/0276489 A1 | 11/2007 | Bindseil et al. | |
| 2008/0206297 A1 | 8/2008 | Roeder et al. | |
| 2009/0022615 A1 | 1/2009 | Entezarian | |
| 2009/0048675 A1 | 2/2009 | Bhatnagar et al. | |
| 2009/0124147 A1 | 5/2009 | Pertez | |
| 2009/0126225 A1 | 5/2009 | Jarvis | |
| 2009/0192609 A1 | 7/2009 | Klabunde et al. | |
| 2009/0312758 A1 * | 12/2009 | Petit | A61B 17/809 606/60 |
| 2010/0070022 A1 | 3/2010 | Kuehling | |
| 2010/0291401 A1 | 11/2010 | Medina et al. | |
| 2011/0008754 A1 | 1/2011 | Bassett et al. | |
| 2011/0014081 A1 | 1/2011 | Jones et al. | |
| 2011/0070358 A1 | 3/2011 | Mauch et al. | |
| 2011/0152865 A1 | 6/2011 | Ralph et al. | |
| 2011/0307053 A1 | 12/2011 | Gale et al. | |
| 2012/0132631 A1 | 5/2012 | Wescott et al. | |
| 2012/0232654 A1 | 9/2012 | Sharp et al. | |
| 2013/0171466 A1 | 7/2013 | Maffia | |
| 2013/0218288 A1 | 8/2013 | Fonte et al. | |
| 2013/0268085 A1 | 10/2013 | Dong et al. | |
| 2013/0325126 A1 | 12/2013 | Bradica et al. | |
| 2013/0325142 A1 | 12/2013 | Hunter et al. | |
| 2014/0037873 A1 | 2/2014 | Cheung et al. | |
| 2014/0128916 A1 | 5/2014 | Williams | |
| 2014/0249643 A1 | 9/2014 | Jones et al. | |
| 2014/0277150 A1 | 9/2014 | Jones et al. | |
| 2015/0032197 A1 | 1/2015 | Bar et al. | |
| 2015/0037601 A1 | 2/2015 | Blackmore | |
| 2015/0045903 A1 | 2/2015 | Neal | |
| 2015/0202047 A1 | 7/2015 | Patterson et al. | |
| 2015/0224710 A1 | 8/2015 | El-Siblani | |
| 2015/0230925 A1 | 8/2015 | Strippgen | |
| 2015/0239046 A1 | 8/2015 | McMahan et al. | |
| 2015/0258735 A1 | 9/2015 | O'Neill et al. | |
| 2015/0265438 A1 | 9/2015 | Hossainy et al. | |
| 2015/0282746 A1 | 10/2015 | Yousefi et al. | |
| 2015/0282945 A1 | 10/2015 | Hunt | |
| 2015/0374521 A1 | 12/2015 | Zheng et al. | |
| 2016/0067375 A1 | 3/2016 | Holmes et al. | |
| 2016/0116267 A1 | 4/2016 | McKendrick | |
| 2016/0157904 A1 | 6/2016 | Zeetser et al. | |
| 2016/0166302 A1 | 6/2016 | Tan-Malecki et al. | |
| 2016/0167312 A1 | 6/2016 | Feinberg et al. | |
| 2016/0175085 A1 | 6/2016 | Johnson et al. | |
| 2016/0199201 A1 | 7/2016 | Weiss et al. | |
| 2016/0199914 A1 | 7/2016 | Potter | |
| 2016/0213403 A1 | 7/2016 | Bowden et al. | |
| 2016/0228608 A1 | 8/2016 | Hakimi et al. | |
| 2016/0287756 A1 | 10/2016 | Lewis et al. | |
| 2016/0338626 A1 | 11/2016 | Wang et al. | |
| 2016/0340542 A1 | 11/2016 | Kim et al. | |
| 2016/0375676 A1 | 12/2016 | Ritchie et al. | |
| 2017/0064840 A1 | 3/2017 | Espalin et al. | |
| 2017/0165790 A1 | 6/2017 | McCarthy et al. | |
| 2017/0218228 A1 | 8/2017 | Jose et al. | |
| 2018/0272607 A1 | 9/2018 | Chaffins et al. | |
| 2018/0361510 A1 | 12/2018 | Stamp et al. | |

FOREIGN PATENT DOCUMENTS

| | | |
|---|---|---|
| DE | 102006047663 A1 | 4/2008 |
| DE | 102006055432 A1 | 5/2008 |
| EP | 0016480 A1 | 10/1980 |
| EP | 0526682 A1 | 2/1993 |
| EP | 1683593 A2 | 7/2006 |
| EP | 2606859 A1 | 6/2013 |
| WO | 03082550 A2 | 10/2003 |
| WO | 2004031086 A1 | 4/2004 |
| WO | 2012078955 A1 | 6/2012 |
| WO | 2013163398 A1 | 10/2013 |
| WO | 2015013479 A2 | 1/2015 |

OTHER PUBLICATIONS

Adam Cohen et al: "Microscale metal additive manufacturing of multi-component medical devices", Rapid Prototyping Journal, vol. 16, No. 3, Apr. 27, 2010 (Apr. 27, 2010), pp. 209-215, XP055704003, GB ISSN: 1355-2546, DOI: 10.1108/13552541011034889.

Aimee, "3D printing custom trachea stents," Shapeways Blog, Aug. 4, 2015, 5 pages, https://www.shapeways.com/blog/archives/21674-3d-printing-custom-trachea-stents.html (retreived on Dec. 9, 2020).

EXETER™ Universal Hip System, Stryker Corporation; Admitted as Prior Art at least as of Dec. 20, 2013; 1 page.

McNichols Industrial Architectural Hole Products Solutions, downloaded from the internet: http://www.mcnichols.com/products/expanded/ on Nov. 12, 2013; 2 pages.

Stamp et al., U.S. Appl. No. 62/520,221 entitled "Porus structures produced by additive layer manufacturing", filed Jun. 15, 2017.

C.K. Chua et al. Development of a Tissue Engineering Scaffold Structure Library for Rapid Prototyping. Parts 1 and 2, International Journal of Advanced Manufacturing Technology, Feb. 2003, vol. 21, pp. 291-312.

Extended European Search Report for Application No. EP16204268.3 dated May 22, 2017.

Liu, "Degradable Scaffold Microstructure of Artificial Bioactive Bone fabricated by 3D Braiding Method", Applied Mechanics and Materials, vol. 610, pp. 980-983, Aug. 1, 2014.

Wang et al., "A Hybrid Geometric Modeling Method for Large Scale Conformal Cellular Structures," ASME Journal of Computing and Information Science in Engineering, 2006, 13 pages.

Deangelis, Stephen, "3D Printing and the Supply Chain", Supply Chain Brief, Enterra Solutions, Mar. 25, 2011, sourced from the web, https://www.enterrasolutions.com/blog/3d-printing-and-the-supply-chain/ on Jan. 7, 2019, 6 pages.

"The Printed World", The Economist, Feb. 10, 2011, acquired from the web, https://www.economist.com/briefing/2011/02/10/the-printed-world?story_id=18114221 on Jan. 7, 2019, 12 pages.

Partial European Search Report for EP18203809.1 dated Mar. 21, 2019.

Search report from Office Action dated Apr. 9, 2019 for Australian Application 2018204211.

Extended European Search Report including Written Opinion for Application No. EP18203809.1 dated Jul. 1, 2019, pp. 1-11.

* cited by examiner

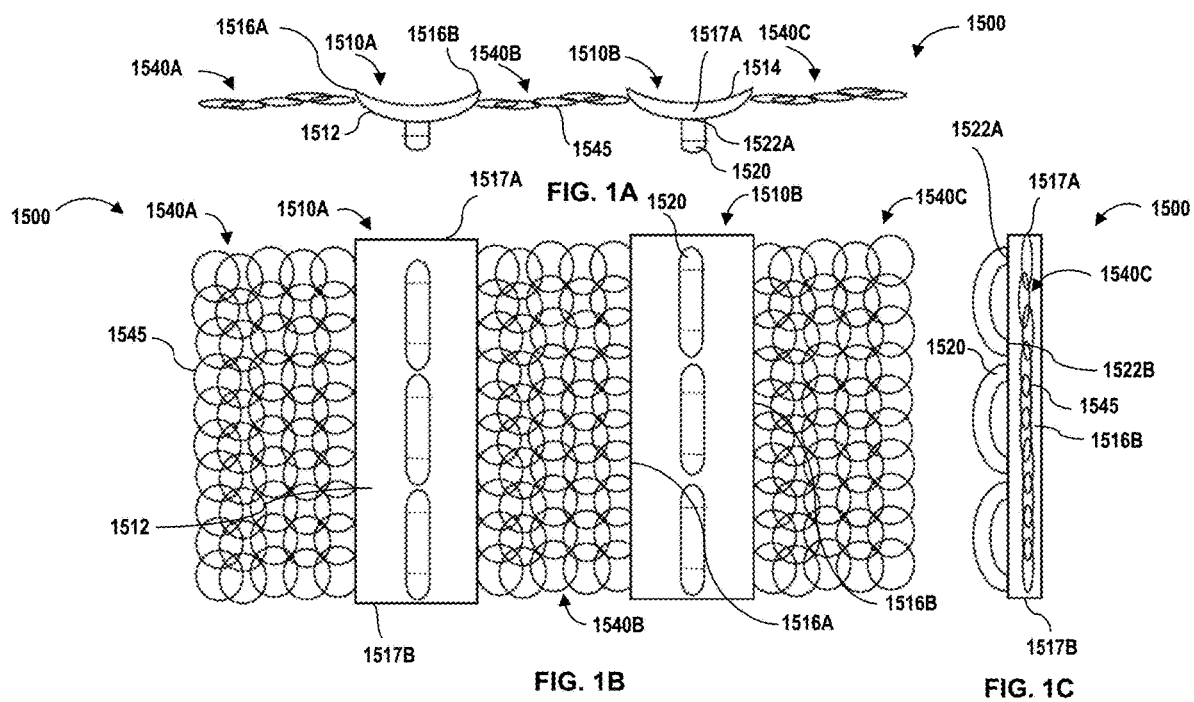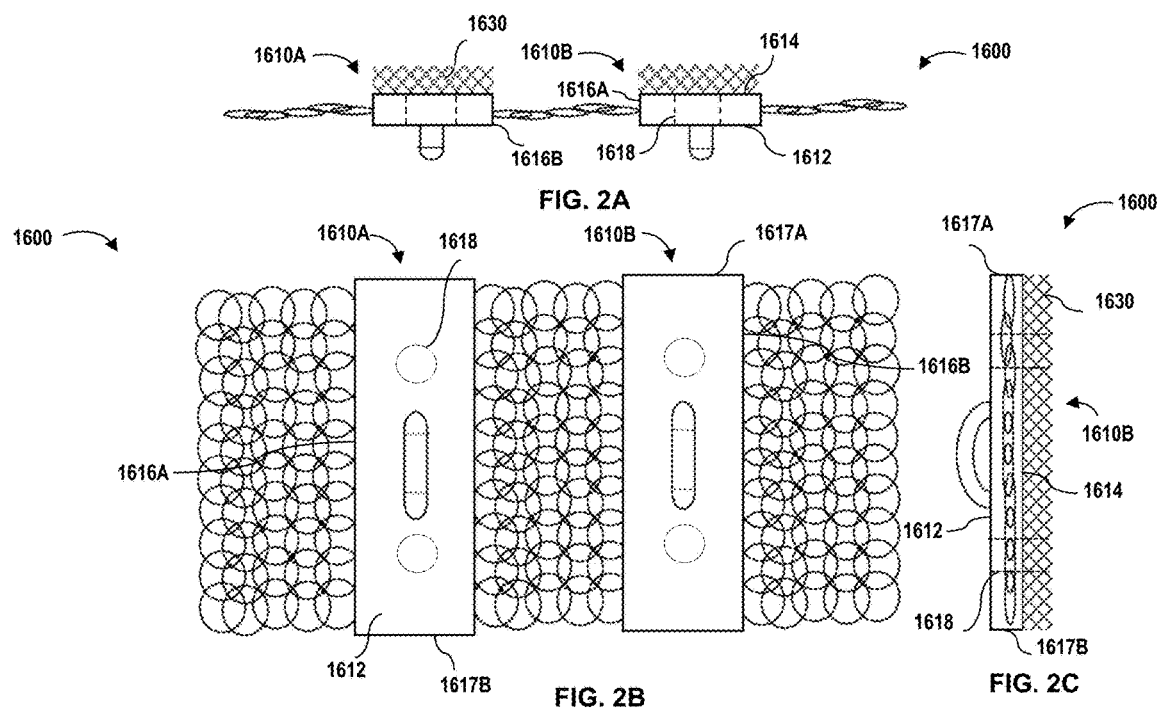

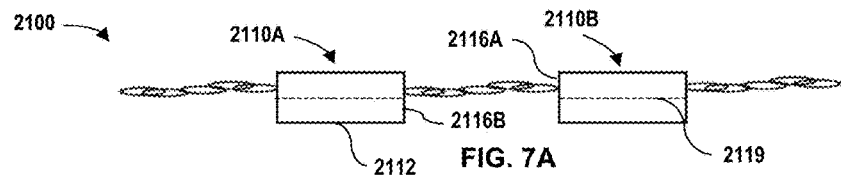
FIG. 7A
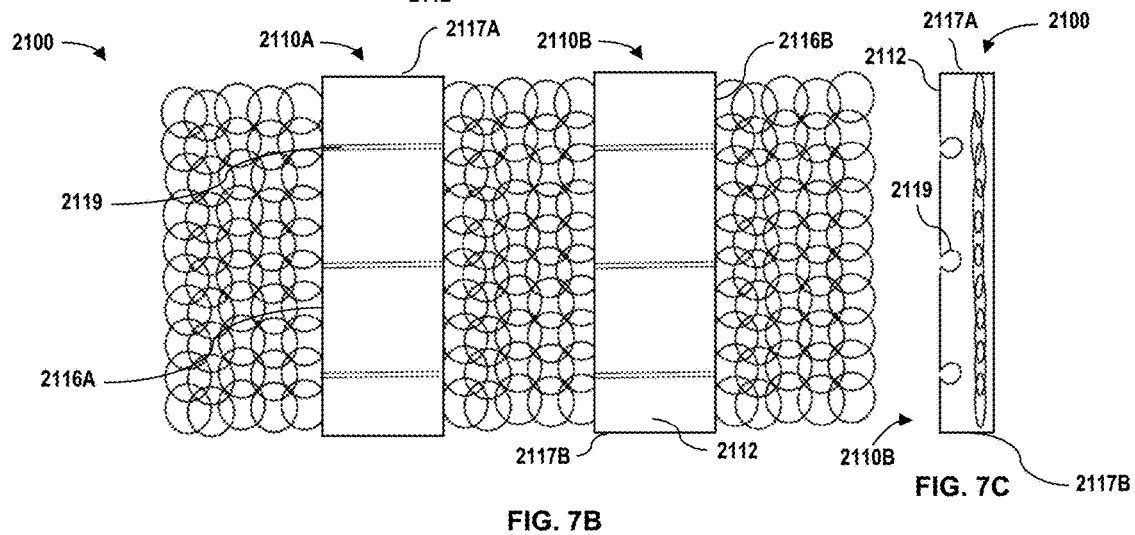
FIG. 7B
FIG. 7C
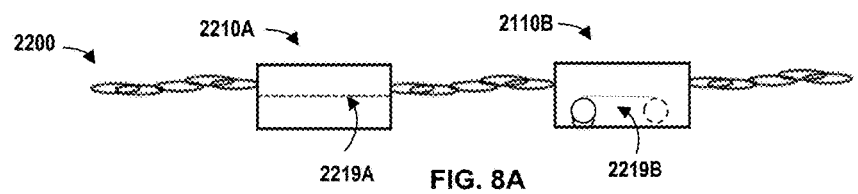
FIG. 8A
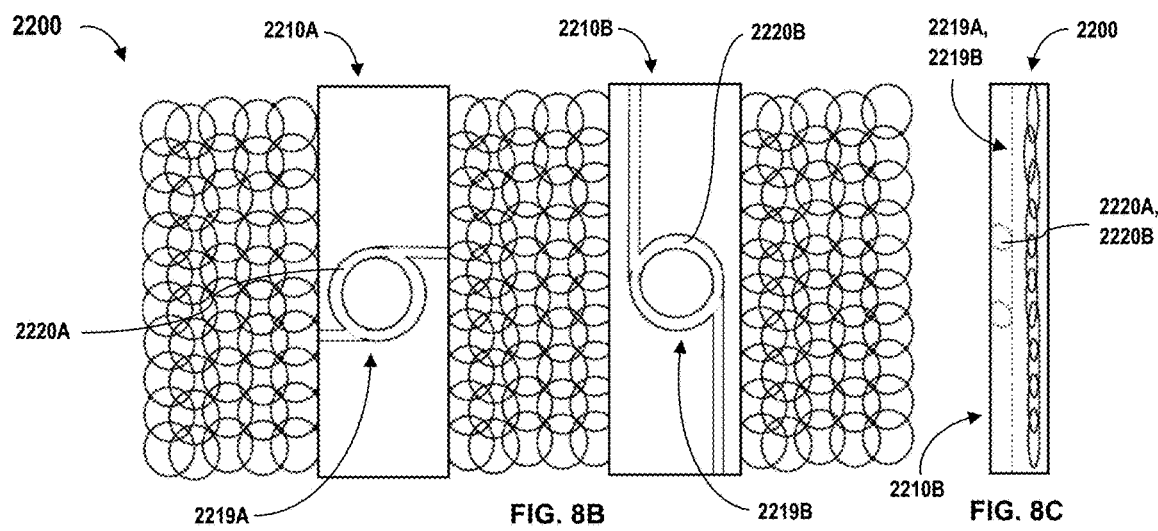
FIG. 8B
FIG. 8C

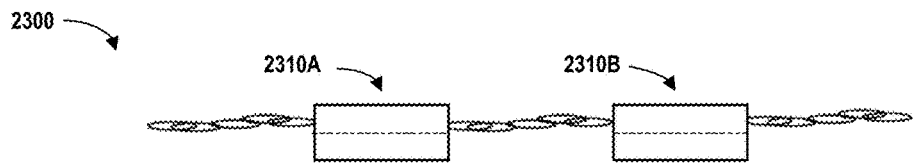
FIG. 9A
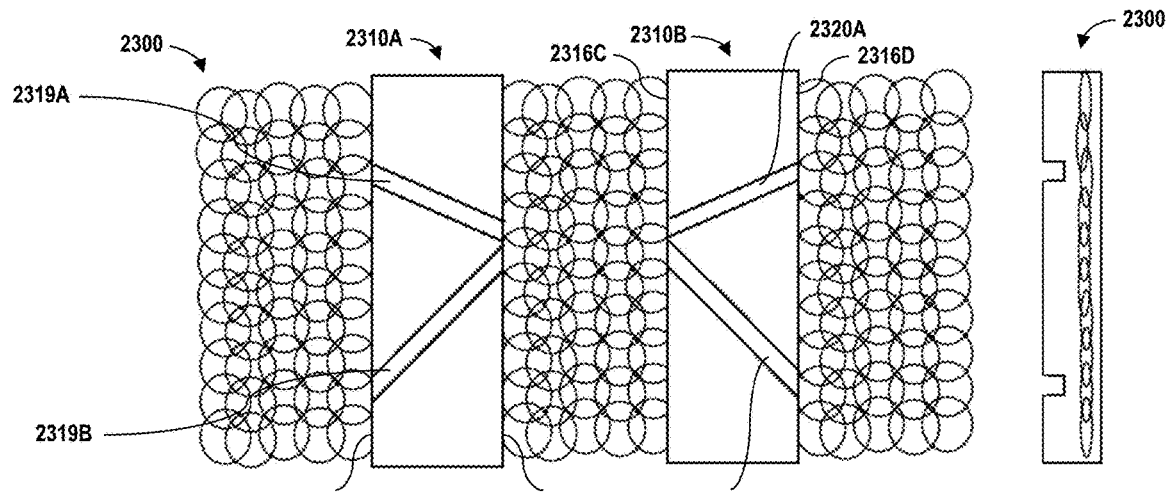
FIG. 9B
FIG. 9C
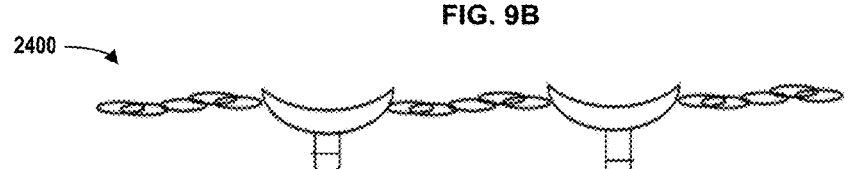
FIG. 10A
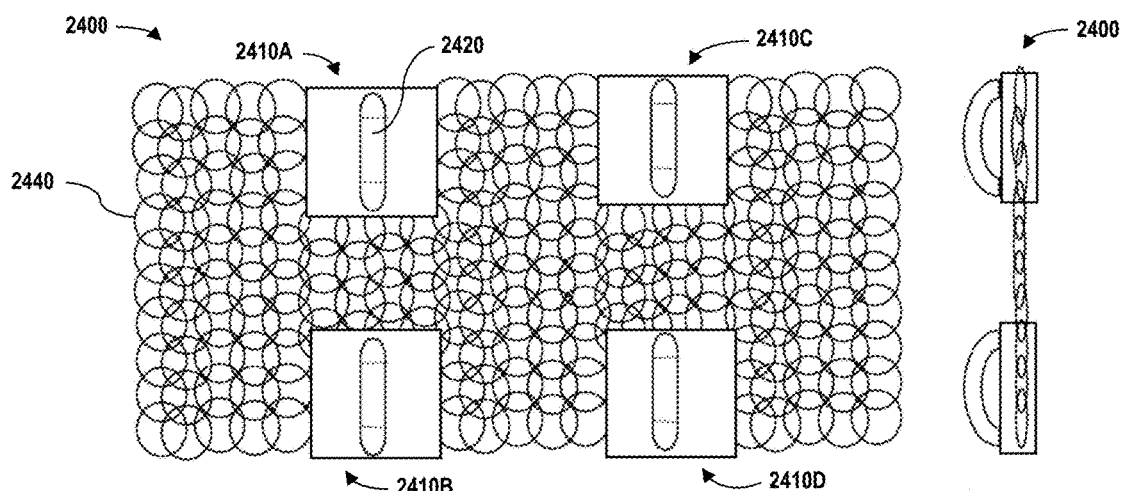
FIG. 10B
FIG. 10C

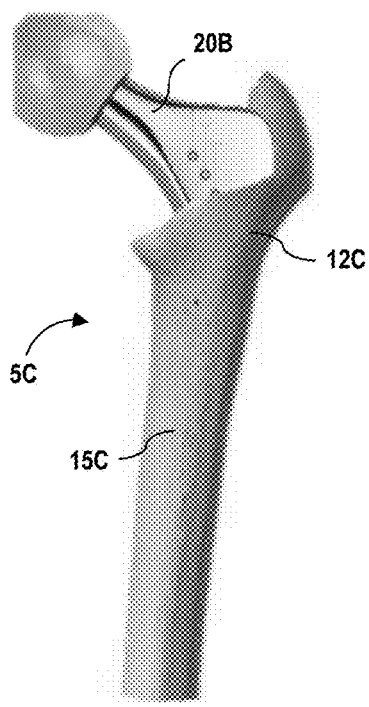 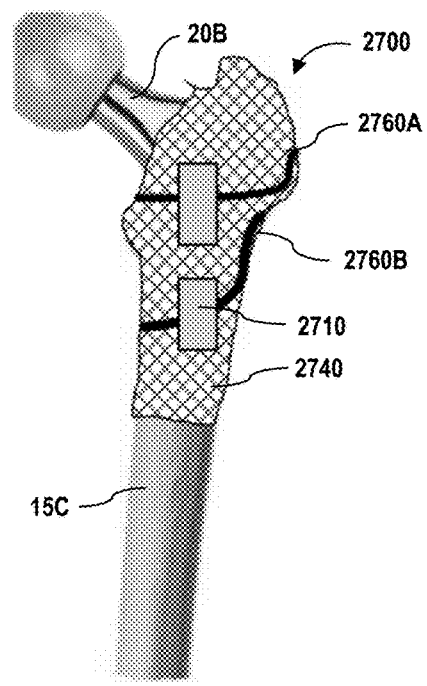
FIG. 13A
FIG. 13B

FLEXIBLE CONSTRUCT FOR FEMORAL RECONSTRUCTION

CROSS-REFERENCE TO RELATED APPLICATION

The present application is a divisional of U.S. patent application Ser. No. 16/177,775 filed Nov. 1, 2018, which claims the benefit of the filing date of U.S. Provisional Application No. 62/581,259 filed Nov. 3, 2017, the disclosures of which are hereby incorporated herein by reference.

FIELD OF THE INVENTION

The present invention relates generally to flexible devices for bone repair, and in particular to features and processes for the attachment of such devices.

BACKGROUND OF THE INVENTION

Examples of modern rapid manufacturing technologies include additive layer manufacturing (ALM) techniques such as electron beam melting, selective laser sintering (SLS), selective laser melting (SLM), and other three-dimensional (3-D) processes. When employing these technologies, articles are produced in layer-wise fashion from a laser-fusible powder that is dispensed one layer at a time. The powder is sintered in the case of SLS technology and melted in the case of SLM technology, by the application of laser energy that is directed in raster-scan fashion to portions of the powder layer corresponding to a cross section of the article. After the sintering or melting of the powder on one particular layer, an additional layer of powder is dispensed, and the process repeated, with sintering or melting taking place between the current layer and the previously laid layers until the article is complete. In one example, a high energy beam is emitted from a beam-generating apparatus to heat metal powder sufficiently to sinter and preferably to at least partially melt or fully melt the metal powder. High energy beam equipment for manufacturing such structures may be one of many commercially available. The beam generation equipment may also be a custom-produced laboratory device. Detailed descriptions of the SLS technology may be found in U.S. Pat. Nos. 4,863,538, 5,017,753, 5,076,869, and 4,944,817, the entire disclosures of which are incorporated by reference herein. Similarly, a detailed description of the use of SLM technology may be found in U.S. Pat. No. 7,537,664 ("the '664 Patent"), the disclosure of which is incorporated by reference herein. The SLM and SLS technologies have enabled the direct manufacture of solid or porous three-dimensional articles of high resolution and dimensional accuracy from a variety of materials including wax, metal and metal alloys, metal powders with binders, polycarbonate, nylon, other plastics and composite materials, such as polymer-coated metals and ceramics.

Other non-powder based additive manufacturing technologies are also known to produce high resolution and dimensionally accurate articles. For example, in fused filament fabrication (FFF) or Plastic Jet Printing (PJP), strands of molten material are extruded from a nozzle to form layers onto a substrate in which the material hardens upon extrusion. Using digital light processing (DLP), photosensitive resin plastic is cured by light and built layer by layer from the bottom-up or a vat of liquid polymer is exposed to balanced levels of ultraviolet light and oxygen to produce a part often from the top-down. In inkjet 3D printing, a liquid binding material is selectively deposited across a thin layer of a powder and the process is repeated in which each new layer is adhered to the previous layer.

The invention claimed in the '664 Patent is one of several commonly owned by Howmedica Osteonics Corporation that relate to additive manufacturing. For instance, U.S. Pat. Appl. Publ. Nos. 2006/0147332 A1 ("the '332 Publication"), U.S. Pat. No. 9,456,901 ("the '901 Patent"), U.S. Pat. No. 8,992,703 ("the '703 Patent"), U.S. Pat. No. 9,135,374 ("the '374 Patent"), and U.S. Pat. No. 9,180,010 ("the '010 Patent"), the entire disclosures of which are hereby incorporated by reference herein, have taught the generation and organization of a population of porous geometry, a mathematical representation of the portion of geometry of the porous structure to be built within a region defined by a predetermined unit cell or imaginary volume, to fill and form a predetermined build geometry, i.e., a model build structure, which may be used to produce a near net-shape of an intended porous tissue in-growth structure. The predetermined build geometry, or overall computer-aided design (CAD) geometry, may refer to the mathematical or pictorial representation (such as that on a computer display) of the intended physical structure to be manufactured. In the case of physical components that include both porous material and solid material, the predetermined build geometry may be an assembly of solid and porous CAD volumes that define the outer boundaries of the respective solid and porous materials intended to be manufactured. Furthermore, these applications teach the randomization of the position of interconnected nodes, or points of intersection between two struts or between a strut and a substrate, that define each of the porous geometries while maintaining the interconnectivity between the nodes. As further taught in these applications, such randomization may be accomplished by changing the coordinate positions of the nodes, in the x, y, and z directions of a Cartesian coordinate system, to new positions based on a defined mathematical function.

Porous medical implants produced using ALM techniques, which typically require the use of biocompatible materials such as titanium, have been built with strong scaffolds, but such implants are too rigid to allow for adequate deformation to either one or both fill void spaces created by bone degradation and conform to existing bone surfaces. As an example, repair of a weakened or fractured trochanter present limitations due to the curvature of the trochanter. In this regard, an extended trochanteric osteotomy (ETO) procedure is often required during hip revision surgery necessitating reattachment of the trochanter and the superior portion of the femur.

Thus, improved implants and procedures are needed to accommodate the repair of curved bone portions, such as trochanters, and in any event ongoing improvements are always needed to improve the fixation of implants to bone.

BRIEF SUMMARY OF THE INVENTION

In accordance with an aspect, a bone repair device may include a plate, a partial loop that may be directly attached to the plate, and a flexible structure that may be directly attached to the plate. The plate may include a top surface, a bottom surface opposite the top surface, and a side surface extending between the top and the bottom surfaces. The partial loop may be attached to the top surface of the plate, and the flexible structure may be attached to the side surface of the plate. The partial loop may include two ends in which either one or both of the ends may attach the partial loop to the plate. In this manner, the partial loop may define a convex interior for surrounding another object, such as a cable that preferably may be a cerclage wire. The flexible structure may be a porous structure. In some arrangements, the porous flexible structure may be formed of a layer of open or closed links, e.g., chain links, connected together in the form of a sheet. Such a sheet layer may have a thickness of a single one of the links in a sheet made of a uniform set of links. In some arrangements, the porous flexible structure may be a woven mesh sheet while, in some other arrangements, the porous flexible structure may be a non-woven mesh sheet. In some arrangements, the flexible structure may be formed of a plurality of layers of such sheets of connected links and mesh sheets.

In some arrangements, all or a portion of the plate may be porous. In some arrangements, the plate may have a varying porosity, which may be a gradient porosity. In some arrangements, holes, which may be threaded holes, may extend through the plate to allow a fastener to be inserted through the holes and into bone for further securement of the plate to bone portions. In some arrangements, the holes may include chamfers or steps for preventing a head of a fastener having a head and shank from passing through the plate upon insertion into the plate. In some arrangements, either one or both of the top surface of the plate and the bottom surface of the plate may be flat. In some arrangements, either one or both of the top surface of the plate may be convex and the bottom surface of the plate may be concave. In some arrangements, suture may be directly attached to, and in some such arrangements may be embedded in the plate. In some such arrangements, the plate may include holes which may be dimensioned to receive suture anchors for attachment with soft tissue.

These various configurations of this aspect of the bone repair device may be sufficiently flexible such that the bone repair device may be wrapped around portions of bone requiring repair that may have varying thicknesses, for example sections of a trochanter of a femur. The bone repair device may be secured to bone portions requiring repair at the time of placement around such bone portions by passing a cerclage wire between the partial loop and the top surface of the plate to which the loop is attached, wrapping the cerclage wire around the bone portions, and then tying off ends of the cerclage wire in a manner known to those skilled in the art.

In accordance with another aspect, a bone repair device may include a plate having a pathway that extends across a length of the plate and a flexible structure that may be directly attached to the plate. In this manner, a cable, which may be a cerclage wire, may be inserted through the pathway of the plate. The plate may include a top surface, a bottom surface opposite the top surface, and a side surface extending between the top and the bottom surfaces. The flexible structure may be attached to the side surface of the plate.

In some arrangements, the pathway may be a channel which may be a hole extending through the side surface of the plate and through a thickness of the plate defined by the side surface. In some arrangements, the pathway may be a recess that extends through a portion of the top surface of the plate such that a portion of the plate below the top surface is exposed. In some such arrangements, the recess may have a regular or irregular cross-sectional profile. In some such arrangements when the recess has a regular cross-sectional profile, such profile preferably may be ovular, circular, rectangular, square, or triangular. In some arrangements, the recess may define an opening having a width that is less than a width of a cable to be inserted into the recess such that the cable must be compressed to be placed into the recess and such that an external force, such as by a user, must be applied to remove the cable from the recess. Alternatively, the recess may define an opening having a width that is greater than a width of a cable to be inserted into the recess. In some arrangements, the pathway may be a combination of a hole extending through the side surface of the plate and a recess extending through a portion of the top surface of the plate.

In some arrangements, the pathway, whether either one or both of a hole or a recess, may extend in a direction perpendicular to the side surface. In some arrangements, the pathway, whether either one or both of a hole or a recess, may extend along an axis that intersects the side surface at an oblique angle. In some arrangements, the pathway, whether either one or both of a hole or a recess, may either one or both of linear and curved along a length of the pathway. In such arrangements, the pathway, whether either one or both of a hole or a recess, may include a circuit such as a "roundabout," whereby a cable placed along the pathway overlaps a portion of itself.

In some arrangements, the flexible structure may be a porous structure. In some arrangements, the porous flexible structure may be formed of a layer of open or closed links, e.g., chain links, connected together in the form of a sheet. Such a sheet layer may have a thickness of a single one of the links in a sheet made of a uniform set of links. In some arrangements, the porous flexible structure may be a woven mesh sheet while, in some other arrangements, the porous flexible structure may be a non-woven mesh sheet. In some arrangements, the flexible structure may be formed of a plurality of layers of such sheets of connected links and mesh sheets.

In some arrangements, all or a portion of the plate may be porous. In some arrangements, the plate may have a varying porosity, which may be a gradient porosity. In some arrangements, holes, which may be threaded holes, may extend through the plate to allow a fastener to be inserted through the holes and into bone for further securement of the plate to bone portions. In some arrangements, the holes may include chamfers or steps for preventing a head of a fastener having a head and shank from passing through the plate upon insertion into the plate. In some arrangements, either one or both of the top surface of the plate and the bottom surface of the plate may be flat. In some arrangements, either one or both of the top surface of the plate may be convex and the bottom surface of the plate may be concave. In some arrangements, suture may be directly attached to, and in some such arrangements may be embedded in the plate. In some such arrangements, the plate may include holes which may be dimensioned to receive suture anchors for attachment with soft tissue.

These various configurations of this aspect of the bone repair device may be sufficiently flexible such that the bone repair device may be wrapped around portions of bone requiring repair that may have varying thicknesses, for example sections of a trochanter of a femur. The bone repair device may be secured to bone portions requiring repair at the time of placement around such bone portions by passing a cerclage wire between the partial loop and the top surface of the plate to which the loop is attached, wrapping the cerclage wire around the bone portions, and then tying off ends of the cerclage wire in a manner known to those skilled in the art.

In accordance with an aspect, a bone repair device may be formed. In forming the bone repair device, a first layer of a material may be deposited onto a substrate. A first layer of the material may be scanned with a high energy beam to at least partially melt the first layer of the material. Successive layers of the material may be deposited onto the first layer. Each of the successive layers of the material may be scanned with the high energy beam at predetermined locations to form at least a first segment, a second segment, and a third segment in which the first segment overlaps the second segment and underlaps the third segment. The first segment, the second segment, and the third segment may form portions of a flexible structure of the bone repair device. The scanned successive layers of the material may form a plate in conjunction with the flexible structure. The plate may include a top surface, a bottom surface opposite the top surface, and a side surface extending between the top and the bottom surfaces. The flexible structure may be attached to the side surface of the plate.

In some arrangements, the scanned successive layers of the material may form a partial loop. In some such arrangements, the plate may be directly attached to the flexible structure and the partial loop. The partial loop may have a configuration such as any of the configurations of partial loops described above or further herein.

In some arrangements, the scanned successive layers of the material may form the plate with a pathway. The pathway may be recess, hole, or other channel which may have configurations such as any of the configurations of respective pathways described above or further herein.

In some arrangements, any number of the segments may be a curvilinear segment. In some arrangements, any number of the segments may be a rectilinear segment. In some arrangements, any number of the segments may include both curvilinear and rectilinear portions.

In some arrangements, the flexible structure of the bone repair device may be in the form of a mesh defined by a weave pattern or a chain-link pattern.

In some arrangements, the material may be any one or any combination of titanium, a titanium alloy, stainless steel, magnesium, a magnesium alloy, cobalt, a cobalt alloy, a cobalt chrome alloy, nickel, a nickel alloy, tantalum, and niobium, polyethylene (PE) and variations thereof, polyetheretherketone (PEEK), polyetherketone (PEK), acrylonitrile butadiene styrene (ABS), silicone, and cross-linked polymers, bioabsorbable glass, ceramics, and biological active materials including collagen/cell matrices.

In some arrangements, when scanning each of the successive layers at predetermined locations a fourth segment spaced from the first segment, underlapping the second segment, and overlapping the third segment may be formed.

In some arrangements, the second and third segments may be spaced from each other.

In some arrangements, the third segment may be the second segment such that the first segment underlaps and overlaps the second segment. In such arrangements, the second and third segments may form part of a link, which may form a portion of a chain mail structure.

In some arrangements, the first segment may completely surround the second segment. In such arrangements, the first segment may be a link of a chain mail structure.

In some arrangements, the second segment may completely surround the first segment. In such arrangements, the second segment may be a link of a chain mail structure.

In some arrangements, when scanning each of the successive layers at predetermined locations a plurality of segments may be formed that may completely surround the first segment.

In some arrangements, a first additional layer of the material may be deposited onto at least a predetermined location of the first segment. In some such arrangements, the first additional layer of the material may be scanned with the high energy beam at the predetermined location of the first segment. In this manner, the first additional layer of the material may be fused to the first segment at the predetermined location.

In some arrangements, successive additional layers of the material may be deposited onto the first additional layer. In some such arrangements, each of the successive additional layers may be scanned with the high energy beam at predetermined locations. In this manner, at least a first additional segment may be formed overlapping a second additional segment and underlapping a third additional segment in which the first additional segment may be fused to at least the first segment at the predetermined location of the first segment.

In some arrangements, the third additional segment may be the second additional segment such that the first additional segment underlaps and overlaps the second additional segment. In such arrangements, the second and third segments may form part of a link, which may form a portion of a chain mail structure.

In some arrangements, when scanning each of the successive additional layers at predetermined locations, a fourth additional segment spaced from the first additional segment, underlapping the second additional segment, and overlapping the third additional segment may be formed.

In some arrangements, when depositing the first additional layer of the material, the first additional layer of the material may be further deposited onto predetermined locations of the second, third, and fourth segments. In some such arrangements, when scanning the first additional layer of the material with the high energy beam, the first additional layer may be fused to each of the second, third, and fourth segments at the respective predetermined locations of the second, third, and fourth segments.

In some arrangements, successive additional layers of the material may be deposited onto the first additional layer. In some such arrangements in which successive additional layers of the material may be deposited onto the first additional layer, each of the successive additional layers may be scanned with the high energy beam at predetermined locations to form at least one symbol. In some such arrangements forming at least one symbol, any number of such symbols may be fused to at least the first segment at the predetermined location of the first segment. In some such arrangements forming at least one symbol, any number of such symbols may be an alphanumeric character.

In some arrangements, when scanning each of the successive layers at predetermined locations, at least one barb may be formed. Any number of such barbs may extend from any one or any combination of the first, second, and third segments.

In some arrangements, when scanning each of the successive layers at predetermined locations, a first series of segments extending in a first direction and a second series of segments extending in a second direction transverse to the first direction may be formed. The first series of segments may include the first segment. The second series of segments may include the second and third segments. Some or all of the segments of the first series of segments may overlap a plurality of segments of the second series of segments and may underlap another plurality of segments of the second series of segments such that the first and second series of segments form a first mesh.

In some arrangements, the first mesh may be a flexible sheet. The first mesh may be foldable such that a substantially planar first portion of the first mesh lies in a plane at an angle of up to substantially 180 degrees to a plane in which a substantially planar second portion of the first mesh lies.

In some arrangements, when scanning each of the successive layers of the material at predetermined locations, a third series of segments extending in a third direction and a fourth series of segments extending in a fourth direction transverse to the third direction may be formed. In some such arrangements, each of the segments of the third series of segments may overlap a plurality of segments of the fourth series of segments and may underlap a plurality of segments of the fourth series of segments. In this manner, the third and fourth series of segments may form a second mesh. In some such arrangements, when scanning each of the successive layers at predetermined locations, at least one segment may be formed that underlaps and overlaps at least one segment of the first and second series of segments and at least one segment of the third and fourth segments such that the first and second meshes may be rotatably attached to each other.

In some arrangements, the first and the third directions are the same. In the same or in other arrangements, the second and the fourth directions are the same.

In some arrangements, either one or both of the first and the second meshes may have a profile substantially in the form of any one or any combination of a square, a rectangle, a circle, and a triangle.

In some arrangements, the first and the second meshes may have edges adjacent and substantially parallel to each other such that upon rotation of either of the edges about the other edge, the edges do not interfere with such rotation.

In some arrangements, pluralities of the segments of the first and second series of segments may define a bore through a thickness of the scanned successive layers of the material.

In some arrangements, when scanning each of the successive layers at predetermined locations, an outer ring may be formed. In some such arrangements when scanning each of the successive layers at predetermined locations, ends of pluralities of the segments of the first and second series of segments may be fused to an outer perimeter of the outer ring. In some such arrangements, an inner perimeter opposite the outer perimeter of the outer ring may define the bore through the thickness of the scanned successive layers of the material.

In some arrangements, when scanning each of the successive layers at predetermined locations, an inner ring concentric with the outer ring may be formed. In some such arrangements when scanning each of the successive layers at predetermined locations, segments fused to and between the inner perimeter of the outer ring and an outer perimeter opposite an inner perimeter of the inner ring may be formed. In such arrangements, the inner perimeter of the inner ring may define the bore through the thickness of the scanned successive layers of the material.

In some arrangements, when scanning each of the successive layers at predetermined locations a stud or rivet may be formed. In some such arrangements, ends of pluralities of the segments of the first and second series of segments may fused to the perimeter of the stud or rivet.

In some arrangements, when scanning each of the successive layers at predetermined locations, a third series of segments extending in a third direction and a fourth series of segments extending in a fourth direction transverse to the third direction may be formed. In some such arrangements, each of the segments of the third series of segments may overlap a plurality of segments of the fourth series of segments and may underlap a plurality of segments of the fourth series of segments. In this manner, the third and fourth series of segments may form a second mesh. In some such arrangements, when scanning each of the successive layers at predetermined locations, a solid section may be formed. The solid section may be fused to each of the first and second meshes. In this manner, the solid section may be movable relative to portions of each of the first and second meshes.

In some arrangements, when scanning each of the successive layers at predetermined locations a hook extending from the first segment may be formed.

In some arrangements, the first segment may be fused to at least one of the second and the third segments.

In some arrangements, the first segment may be fused to only one of the second and the third segments.

In accordance with another aspect, bone ingrowth may be facilitated. In facilitating such bone ingrowth, a porous tissue ingrowth structure may be formed in the shape of a bone repair device including a plate defining a pathway and a flexible structure attached to the plate. In forming the bone repair device, a first layer of a material may be deposited onto a substrate. A first layer of the material may be scanned with a high energy beam to at least partially melt the first layer of the material. Successive layers of the material may be deposited onto the first layer. Each of the successive layers of the material may be scanned with the high energy beam at predetermined locations to form at least a first segment, a second segment, and a third segment in which the first segment overlaps a second segment and underlaps a third segment. At least the first segment, the second segment, and the third segment may form portions of the flexible structure of the bone repair device. At least the flexible structure of the bone repair device may be shaped into a desired shape. At least the flexible structure of the bone repair device may have a porosity to promote bone ingrowth. The bone repair device may be placed against one or more bone portions. A cable may be inserted through the pathway defined by the plate and may be wrapped around the flexible structure and the bone portions. In some arrangements, the plate may be porous.

In accordance with another aspect, a bone repair device may be formed. In forming the bone repair device, a first layer of a material may be formed over at least a substrate. The first layer of the material may be scanned with a high energy beam to form a first pattern. The first pattern may include a first portion (a1) of a first solid portion (A). A second layer of the material may be deposited over the first layer of the material. The second layer of the material may be scanned with a high energy beam to form a second pattern. The second pattern may include a first portion (b1) of a second solid portion (B). A third layer of the material may be deposited over at least a substrate. The third layer of the material may be scanned with a high energy beam to form a third pattern. The third pattern may include a second portion (a2) of the first solid portion (A). A fourth layer of the material may be deposited over at least the second layer of the material. The fourth layer of the material may be scanned with a high energy beam to form a fourth pattern. The fourth pattern may include a third portion (a3) of the first solid portion (A). A fifth layer of the material may be deposited over at least the third layer of the material. The fifth layer of the material may be scanned with a high energy beam to form a fifth pattern. The fifth pattern may include a first portion (c1) of a third solid portion (C). A sixth layer of the material may be deposited over at least the fifth layer of the material. The sixth layer of the material may be scanned with a high energy beam to form a sixth pattern. The sixth pattern may include a fourth portion (a4) of the first solid portion (A). The first, second, third, and fourth portions of the first solid portion (A) may be attached to each other such that the first solid portion (A) at least partially wraps around the second solid portion (B) and the third solid portion (C). The combination of the first pattern, the second pattern, the third pattern, the fourth pattern, the fifth pattern, and the sixth pattern may form at least portions of a flexible structure of the bone repair device attached to a plate defining a pathway of the bone repair device.

In some arrangements, at least some of the second, third, fourth, and fifth layers may be the same layer.

In some arrangements, the second solid portion (B) is the same as the third solid portion (C) such that the first solid portion (A) forms a link.

In some arrangements, the first and third layers may be the same layer such that the third pattern is part of the first pattern. In such arrangements, the first pattern may further include a first portion (d1) and a second portion (d2) of a fourth solid portion (D). The first portion (d1) and the second portion (d2) of the fourth solid portion (D) may be offset from the first portion (a1) and the second portion (a2) of the first solid portion (A) within the first pattern. In such arrangements, the second and fifth layers may be the same layer such that the fifth pattern is part of the second pattern. In such arrangements, the first portion (b1) of the second solid portion (B) and the first portion (c1) of the third solid portion (C) may be offset from each other. In such arrangements, the fourth and sixth layers may be the same layer such that the sixth pattern is part of the fourth pattern. In such arrangements, the fourth pattern may further include a third portion (d3) and a fourth portion (d4) of the fourth solid portion (D). In such arrangements, the third portion (d3) and the fourth portion (d4) of the fourth solid portion (D) may be offset from the third portion (a3) and the fourth portion (a4) of the first solid portion (A) within the fourth pattern. In such arrangements, the first, second, third, and fourth portions of the fourth solid portion (D) may be attached to each other such that the fourth solid portion (A) weaves around the second solid portion (B) and the third solid portion (C) in the opposite manner that the first solid portion weaves around the second solid portion (B) and the third solid portion (C).

In some arrangements, at least one of the second portion (a2) and the third portion (a3) of the first solid portion (A) may be fused to at least one of the first portion (b1) of the second solid portion (B) and the first portion (c1) of the third solid portion (C).

In accordance with another aspect, a non-transitory computer-readable storage medium may have computer readable instructions of a program stored on the medium. The instructions, when executed by a processor, cause the processor to perform a process of preparing a computer-generated model of a bone repair device including at least a flexible structure constructed of unit cells and a plate directly attached to the flexible structure and defining a pathway. In performing the process, a computer-generated component file may be prepared. The computer-generated component file may include a porous CAD volume which may have a boundary. A space may be populated, by a processor, to include the porous CAD volume. The porous CAD volume may be populated with unit cells. Each of the unit cells may be populated, by a processor, with at least one segment geometry to form a plurality of segment geometries. A first segment geometry of the plurality of segment geometries may overlap a second segment geometry of the plurality of segment geometries and underlap a third segment geometry of the plurality of segment geometries. The first segment, the second segment, and the third segment may form portions of the flexible structure of the bone repair device.

In accordance with another aspect, a bone repair device including a flexible structure and a plate may be formed. In forming the bone repair device, successive layers of a first material may be deposited. At least a portion of each of the deposited layers of the first material may be at least partially melted at predetermined locations to form the flexible structure. Successive layers of a second material may be deposited. At least a portion of each of the deposited layers of the second material may be at least partially melted at additional predetermined locations to form the plate such that the plate is attached to the flexible structure at an intersection and such that the plate defines a pathway. The plate may include a top surface, a bottom surface opposite the top surface, and a side surface extending between the top and the bottom surfaces. The flexible structure may be attached to the side surface of the plate.

In some arrangements, the pathway may be a channel which may be a hole extending through the side surface of the plate and through a thickness of the plate defined by the side surface. In some arrangements, the pathway may be a recess that extends through a portion of the top surface of the plate such that a portion of the plate below the top surface is exposed. In some such arrangements, the recess may have a regular or irregular cross-sectional profile. In some such arrangements when the recess has a regular cross-sectional profile, such profile preferably may be ovular, circular, rectangular, square, or triangular. In some arrangements, the recess may define an opening having a width that is less than a width of a cable to be inserted into the recess such that the cable must be compressed to be placed into the recess and such that an external force, such as by a user, must be applied to remove the cable from the recess. Alternatively, the recess may define an opening having a width that is greater than a width of a cable to be inserted into the recess. In some arrangements, the pathway may be a combination of a hole extending through the side surface of the plate and a recess extending through a portion of the top surface of the plate.

In some arrangements, the pathway, whether either one or both of a hole or a recess, may extend in a direction perpendicular to the side surface. In some arrangements, the pathway, whether either one or both of a hole or a recess, may extend along an axis that intersects the side surface at an oblique angle. In some arrangements, the pathway, whether either one or both of a hole or a recess, may either one or both of linear and curved along a length of the pathway. In such arrangements, the pathway, whether either one or both of a hole or a recess, may include a circuit such as a "roundabout," whereby a cable placed along the pathway overlaps a portion of itself.

In some arrangements, the successive layers of the first and the second materials may be at least partially melted with a high energy beam. In some arrangements, the either one or both of the first and the second materials may be made of any one or any combination of plastic, metal, ceramic, and glass. In some arrangements, either one or both of the first and the second materials may be a superelastic metal alloy. In some arrangements, the first material and the second material may be the same material. In some arrangements, either one or both of the first and the second materials may be powder.

In some arrangements, portions of a plurality of segments may be formed when the deposited layers of either one or both of the first and the second materials are at least partially melted. In some such arrangements, the formed segments of the plurality of segments may be attached to at least one other formed segment of the plurality of segments at vertices to define either one or both of a plurality of open cells and a plurality of links, e.g. chain links as described above and further herein. In some such arrangements, the plurality of open cells may form a surface or surfaces of either of or both the flexible structure and the plate. In some arrangements, the open cells may form a reticulated configuration. In some arrangements, the open cells may be tessellated. In some arrangements, each of the plurality of the segments may have opposing ends. In some arrangements, each of the open cells may be bounded by a respective closed perimeter defined by only attached pairs of segments of the plurality of segments. In some arrangements, some of the open cells may be larger than some of the other open cells.

In some arrangements, the first material and the second material may be the same material. In some arrangements, a fully dense region of the first material may be formed between open cells of the plurality of open cells in the flexible structure when the deposited layers of the first material are at least partially melted.

In some arrangements, the segments of the plurality of segments may have a diameter of less than 200 µm. In some such arrangements, the segments of the plurality of segments may have a diameter in the range from 10 to 150 µm. In some arrangements, the flexible structure and the plate may share segments of the plurality of segments at their intersection.

In some arrangements, projections extending from either of or both the flexible structure and the plate may be formed when the respective deposited layers of either one or both of the first and the second materials are at least partially melted. In some such arrangements, at least some of the projections may be curved struts.

In some arrangements, at least one portion of the flexible structure and at least one portion of the plate may be formed when the deposited layers of the first and the second materials are at least partially melted.

In some arrangements, either of or both the flexible structure and the plate may have varying surface topologies.

In some arrangements, an additional material different from the first material may be deposited with or within at least one of the deposited layers of the first material. In such arrangements, at least a portion of the deposited additional material may be at least partially melted at predetermined marker locations to form radiopaque markers. In some such arrangements, the radiopaque markers, upon formation of the flexible structure and the plate, may be on or extend from either of or both the flexible structure and the plate. In some such arrangements, the additional material may include a predetermined amount of platinum corresponding to a desired level of radiopacity of the radiopaque markers.

In some arrangements, either one or both of the flexible tube and the plate may be formed to interface with another medical device. In some such arrangements, the medical device may be a cerclage wire or a bone screw.

In some arrangements, the first material and the second material may be deposited over a substrate. In some arrangements, e.g., in a "top-down" approach where formed layers may be suspended from an object carrier, later layers of the successively deposited layers that have been at least partially melted may be below earlier such layers relative to the ground.

In accordance with another aspect, a bone repair device including a flexible structure and a plate may be formed. In forming the bone repair device, a first layer of a material may be deposited onto a substrate. At least part of the first layer of the material may be at least partially melted at predetermined locations. Successive layers of the material may be deposited onto previous layers of the material. At least part of each of the successive layers of the material may be at least partially melted at additional predetermined locations to form a flexible structure intersected with a plate in which the flexible structure includes at least a first segment overlapping a second segment and underlapping a third segment and in which the plate defines a pathway. The plate may include a top surface, a bottom surface opposite the top surface, and a side surface extending between the top and the bottom surfaces. The flexible structure may be intersected with the side surface of the plate.

In some arrangements, the third segment may be the second segment such that the first segment underlaps and overlaps the second segment. In some such arrangements, the first segment may completely surround the second segment. In some such arrangements, the second segment may completely surround the first segment.

In some arrangements, the pathway may be a channel which may be a hole extending through the side surface of the plate and through a thickness of the plate defined by the side surface. In some arrangements, the pathway may be a recess that extends through a portion of the top surface of the plate such that a portion of the plate below the top surface is exposed. In some such arrangements, the recess may have a regular or irregular cross-sectional profile. In some such arrangements when the recess has a regular cross-sectional profile, such profile preferably may be ovular, circular, rectangular, square, or triangular. In some arrangements, the recess may define an opening having a width that is less than a width of a cable to be inserted into the recess such that the cable must be compressed to be placed into the recess and such that an external force, such as by a user, must be applied to remove the cable from the recess. Alternatively, the recess may define an opening having a width that is greater than a width of a cable to be inserted into the recess. In some arrangements, the pathway may be a combination of a hole extending through the side surface of the plate and a recess extending through a portion of the top surface of the plate.

In some arrangements, the pathway, whether either one or both of a hole or a recess, may extend in a direction perpendicular to the side surface. In some arrangements, the pathway, whether either one or both of a hole or a recess, may extend along an axis that intersects the side surface at an oblique angle. In some arrangements, the pathway, whether either one or both of a hole or a recess, may either one or both of linear and curved along a length of the pathway. In such arrangements, the pathway, whether either one or both of a hole or a recess, may include a circuit such as a "roundabout," whereby a cable placed along the pathway overlaps a portion of itself.

In accordance with another aspect, a bone repair device including a flexible structure and a plate may be formed. In forming the bone repair device, a first layer of a material may be deposited onto a substrate. At least part of the first layer of the material may be at least partially melted at predetermined locations. Successive layers of the material may be deposited onto previously deposited and at least partially melted layers of the material. At least part of each of the successive layers of the material may be at least partially melted at additional predetermined locations to form a flexible structure intersected with plate. The plate may include a top surface, a bottom surface opposite the top surface, and a side surface extending between the top and the bottom surfaces. The flexible structure may be intersected with the side surface of the plate.

In some arrangements, the pathway may be a channel which may be a hole extending through the side surface of the plate and through a thickness of the plate defined by the side surface. In some arrangements, the pathway may be a recess that extends through a portion of the top surface of the plate such that a portion of the plate below the top surface is exposed. In some such arrangements, the recess may have a regular or irregular cross-sectional profile. In some such arrangements when the recess has a regular cross-sectional profile, such profile preferably may be ovular, circular, rectangular, square, or triangular. In some arrangements, the recess may define an opening having a width that is less than a width of a cable to be inserted into the recess such that the cable must be compressed to be placed into the recess and such that an external force, such as by a user, must be applied to remove the cable from the recess. Alternatively, the recess may define an opening having a width that is greater than a width of a cable to be inserted into the recess. In some arrangements, the pathway may be a combination of a hole extending through the side surface of the plate and a recess extending through a portion of the top surface of the plate.

In some arrangements, the pathway, whether either one or both of a hole or a recess, may extend in a direction perpendicular to the side surface. In some arrangements, the pathway, whether either one or both of a hole or a recess, may extend along an axis that intersects the side surface at an oblique angle. In some arrangements, the pathway, whether either one or both of a hole or a recess, may either one or both of linear and curved along a length of the pathway. In such arrangements, the pathway, whether either one or both of a hole or a recess, may include a circuit such as a "roundabout," whereby a cable placed along the pathway overlaps a portion of itself.

In accordance with another aspect, a bone repair device, which may be a non-biological strut graft, includes a plate, a first partial loop, and a first flexible structure. The plate may include opposing top and bottom surfaces and a first side extending between the top and the bottom surfaces of the plate. The first partial loop may be attached to the top surface of the plate. The first flexible structure may be directly attached to and may extend from the first side of the plate.

In some arrangements, the partial loop may have two ends. In some such arrangements, only one of the ends of the first partial loop may be attached to the plate. In other such arrangements, both ends of the first partial loop may be attached to the plate.

In some arrangements, the bone repair device may include a second partial loop that may be attached to the top surface of the plate.

In some arrangements, the first flexible structure may be porous. In this manner, the first flexible structure may provide for desired bone ingrowth. In some such arrangements, the first flexible structure may be defined by porous geometries. In some arrangements, the porous first flexible structure may be a mesh. In some such arrangements, the mesh may be woven while in other such arrangements the mesh may be non-woven or a combination of woven and non-woven. In some arrangements, the porous first flexible structure may be in the form of chain mail.

In some arrangements, at least a portion of the plate may be porous. In some such arrangements, the plate may be defined by porous geometries.

In some arrangements, at least the bottom surface of the plate may be curved. In some arrangements, a cross-section of the plate within a plane passing through a longitudinal axis defined by the first partial loop may be curved.

In some arrangements, a suture may be attached to the plate. In some such arrangements, the suture may be embedded in the plate. In some arrangements, the bone repair device may include a suture anchor which may be inserted into a hole extending through a thickness of the plate.

In some arrangements, the bone repair device may include a second side and a second flexible structure. The second side may extend between the top and the bottom surfaces of the plate and may oppose the first side of the plate. The second flexible structure may extend from the second side of the plate.

In some arrangements, the bone repair device may include a porous structure that may extend from the bottom surface of the plate. In some such arrangements, the plate may be solid.

In some arrangements, the plate, the first partial loop, and an end of the first flexible structure may be integral with each other such that they are inseparable, and in particular, inseparable without fracture.

In accordance with an aspect, a bone repair device may include a plate and a flexible structure. The plate may include opposing top and bottom surfaces, a first side that may extend between the top and the bottom surfaces, and a pathway that may extend across a length of the plate. The flexible structure may be directly attached to and may extend from the first side of the plate.

In some arrangements, the pathway may be a channel inset from the top surface of the plate such that the channel forms an exposed surface extending across a length of the plate. In some such arrangements, the channel may be an "open channel," exposed at its ends and along a central portion of the channel.

In some arrangements, the pathway may be a recess that may extend through the plate and that may intersect the first side of the plate.

In some arrangements, the pathway may be a channel that may extend through the plate and that may intersect the first side of the plate. In some such arrangements, the channel may be a "closed channel" in which the channel is open only at its ends.

In some arrangements, the pathway may extend at an oblique angle to the first side of the plate.

In some arrangements, the pathway may include a loop and linear portions that may extend from the loop. In some such arrangements, at least one of the linear portions may intersect the first side of the plate.

In some arrangements, the bone repair device may include an additional pathway that may extend across a length of the plate.

In some arrangements, the flexible structure may be porous. In some such arrangements, the porous flexible structure may be a mesh. In some such arrangements, the mesh may be woven while in other such arrangements the mesh may be non-woven or a combination of woven and non-woven. In some arrangements, the porous flexible structure may be in the form of chain mail.

In some arrangements, the plate may be porous. In some such arrangements, the plate may be defined by porous geometries.

In some arrangements, at least the bottom surface of the plate may be curved. In some arrangements, a cross-section of the plate within a plane passing through the pathway may be curved.

In some arrangements, a suture may be attached to the plate. In some such arrangements, a suture may be embedded in the plate. In some arrangements, a suture anchor may be inserted into a hole through a thickness of the plate.

In some arrangements, the bone repair device may include a second side and a second flexible structure. The second side may extend between the top and the bottom surfaces of the plate and may oppose the first side of the plate. The second flexible structure may extend from the second side of the plate.

In some arrangements, the bone repair device may include a porous structure extending from the bottom surface of the plate.

In some arrangements, the plate and an end of the flexible structure may be integral with each other such that they are inseparable, and in particular, may be inseparable without fracture.

In accordance with another aspect, a surgical method may include a sequence of steps. In one step, a bone repair device including a plate and a flexible structure may be placed around and over a plurality of bone parts. The plate may include opposing top and bottom surfaces and a first side that may extend between the top and the bottom surfaces of the plate. The flexible structure may extend from the first side of the plate. The plate may be secured to the plurality of bone parts. The plate may be secured by inserting a cable inserted through a pathway defined by the plate of the bone repair device and then by wrapping the cable around the bone parts.

In some arrangements, the cable may be inserted through the pathway defined by the plate of the bone repair device. In some such arrangements, the cable may be inserted through the pathway by inserting the cable through an opening in the top surface. In some arrangements, the cable may be inserted through the pathway at an oblique angle to the first side. In some arrangements, the cable inserted through the pathway may be wrapped around the bone parts. In some arrangements, the cable may be a cerclage wire or a plurality of cerclage wires.

In accordance with another aspect, a bone repair system may include a bone device and a cable extending through the pathway. The bone device may include a porous plate, a mesh flexible structure, and a porous structure. The porous plate may include a convex top surface, a concave bottom surface that may oppose the top surface, a first side that may extend between the top and the bottom surfaces, and a pathway that may extend across a length of the plate. The mesh flexible structure may be in the form of chain mail in which the flexible structure may be directly attached to and may extend from the first side of the plate. The porous structure may extend from the bottom surface of the plate. The plate, the flexible structure, and the porous structure may be integral with each other such that they are inseparable, and in particular, inseparable without fracture.

BRIEF DESCRIPTION OF THE DRAWINGS

A more complete appreciation of the subject matter of the present invention and the various advantages thereof can be realized by reference to the following detailed description, in which reference is made to the following accompanying drawings:

FIGS. 1A-10C are various views of bone repair devices in accordance with various embodiments;

FIG. 13A is a perspective view of a trochanter as it may be weakened during a hip implantation or through bone remodeling with time;

FIG. 13B is a perspective view of a bone repair device placed onto the weakened trochanter of FIG. 13A in accordance with an embodiment;

DETAILED DESCRIPTION

Figure 3A:
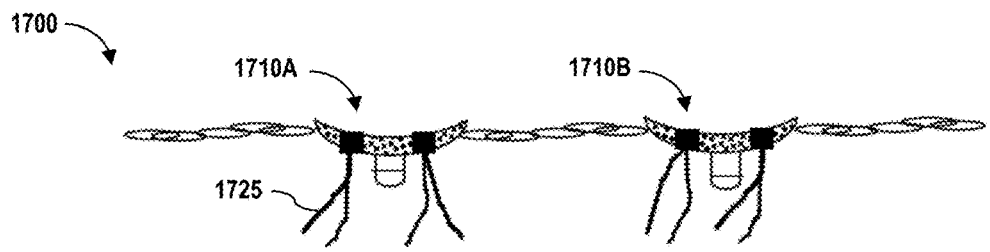

This invention relates generally to flexible devices for bone repair as well as to the preparation and implantation of such devices. In preferable arrangements, such devices may be prepared by additive manufacturing techniques, and in some arrangements, at least a portion of such devices may be patient-specific.

Referring now to FIGS. 1A-1C, bone repair device 1500, which may be termed a "non-biological strut graft," includes a plurality of plates 1510A, 1510B and a plurality of flexible structures 1540A-1540C directly attached to extending from at least one of the plates. In a similar manner to that described further herein with respect to FIGS. 11A, 11B, 12A, 12B, bone repair device 1500 may be secured to a plurality of bone parts of a fractured, resected, or otherwise severed bone, e.g., the femur, to initiate osseointegration, i.e., bone ingrowth, and eventual fusion of the bone parts to repair the bone.

In this example, flexible structure 1540A is attached only to plate 1510A, flexible structure 1540B is attached to and extends between both plate 1510A and plate 1510B, and flexible structure 1540C is attached only to plate 1510B. In some arrangements, additional flexible structures 1540B may be attached to and extend between additional plates 1510A, 1510B. As in this example, plates 1510A, 1510B may be solid or substantially solid. Flexible structures 1540A-1540C are made of intersecting links 1545 in the form of "chain mail." As shown in this example, intersecting links 1545 may be in the form of circles, although in alternative arrangements such links may be in the form of other shapes as described further herein, which preferably may be formed in similar manner that links corresponding to link geometries 455A, 455B described further herein are formed. As further shown in this example, each of links 1545 spaced from the edge, i.e., that do not define an edge, of the flexible structure intersect eight other links. In this manner, intersecting links 1545 remain evenly and uniformly spaced apart within flexible structures 1540A-1540C. In the example shown, intersecting links 1545 define single layers of the links to enhance the flexibility of flexible structures 1540A-1540C. As in this example, the single layers of links 1545 may be generally thinner than sides 1516A, 1516B, 1517A, 1517B of plates 1510A, 1510B.

As further shown, plates 1510A, 1510B include convex top surface 1512 and opposing concave bottom surface 1514 attached to and spaced from the top surface by the plurality of sides 1516A, 1516B, 1517A, 1517B. In this manner, concave bottom surfaces 1514 of plates 1510A, 1510B may more closely conform to a bone to be repaired than alternative plates having a flat bottom surface, and plates 1510A, 1510B may have a thinner radial profile than alternative plates having a flat top surface due to the convexity of top surface 1512.

Each of plates 1510A, 1510B includes a plurality of partial loops 1520 having opposing ends 1522A, 1522B that are attached to and extend from top surface 1512 of each of the plates. As shown, each partial loop 1520 may extend in an arc-fashion to define a pathway between the partial loop and top surface 1512 of plate 1510A, 1510B. In this manner, one or more cables which preferably may be a cerclage wire, may be inserted between partial loop 1520 and top surface 1512 of either one or both of plates 1510A, 1510B, in a similar manner as further described herein with respect to FIGS. 11A, 11B, 13A, 13B. In this manner bone repair device 1500 may be secured to bone parts of bone needed fracture repair. For example, one cable may be inserted between partial loop 1520 and top surface 1512 of plate 1510A and another cable may be inserted between partial loop 1520 and top surface 1512 of plate 1510B.

In another example, as shown in FIGS. 2A-2C, bone repair device 1600 is the same or substantially similar to bone repair device 1500 with the exception that bone repair device 1600 includes a plurality of plates 1610A, 1610B in place of the plurality of plates 1510A, 1510B. Plates 1610A, 1610B are the same or substantially similar to plates 1510A, 1510B with the exception that plates 1610A, 1610B include flat top surface 1612 and opposing flat bottom surface 1614 attached to and spaced from the top surface by the plurality of sides 1616A, 1616B, 1617A, 1617B in place of top surface 1512, bottom surface 1514, and the plurality of sides 1516A, 1516B, 1517A, 1517B, respectively and further include at least one porous structure 1630 extending from bottom surface 1614 and a plurality holes 1618 extending through a thickness of the plates. The plurality of holes 1618 may be at least partially threaded such that a screw may be threaded into the plate, including in this example through porous structure 1630, and into a bone or bone part to secure the plate to the bone or bone part. Porous structure 1630 may have a pore size in the range of approximately 10-1000 µm, and preferably approximately 40-60 µm, and more preferably approximately 50 µm, and may have a porosity in the range of approximately 30% to 90%, and preferably at least 40%, and more preferably approximately 70% such that when the structure is placed against a bone, such porosity allows for bone ingrowth into the pores of the structure to further secure plates 1610A, 1610B against the bone for long-term bone fixation. The porosity of porous structure 1630 preferably may be defined by porous geometries, such as those shown and described in the '374 Patent and the '010 Patent, or may be random as desired. Porous structure 1630 may have a varying porosity, which may be a gradient porosity, throughout a portion or portions of the structure. As in the example shown, porous structure 1630 may extend across the entirety of bottom surface 1614 of each of plates 1610A, 1610B, although in alternative arrangements, one or more such porous structures may extend only across a portion of bottom surface 1614 of any of the plates of the bone repair device depending on the needed interface of the plates with bone to provide the appropriate fixation.

Figure 3B:
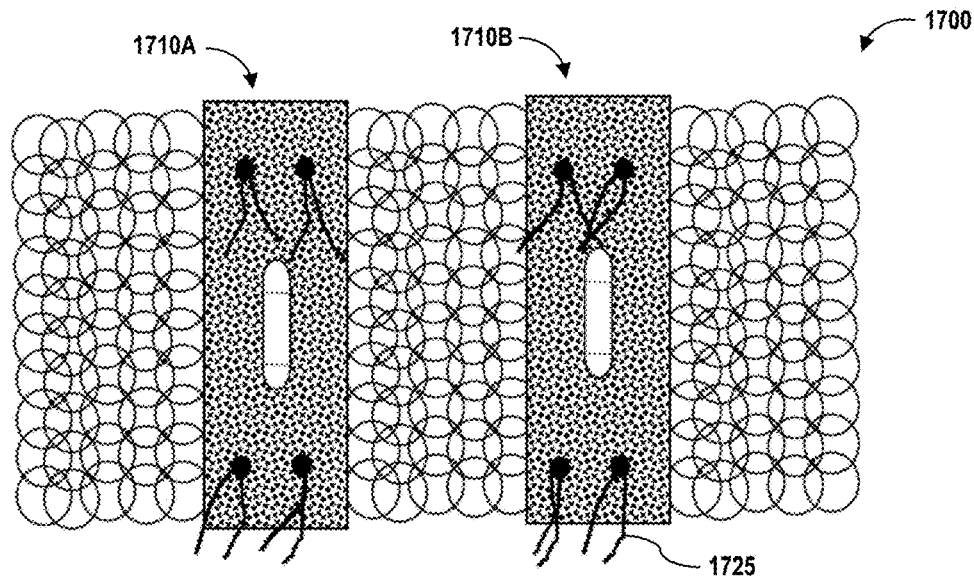

Referring now to FIGS. 3A and 3B, bone repair device 1700 is the same or substantially similar to bone repair device 1500 with the exception that bone repair device 1700 includes a plurality of plates 1710A, 1710B in place of the plurality of plates 1510A, 1510B. Plates 1710A, 1710B are the same or substantially similar to plates 1510A, 1510B with the exception that plates 1710A, 1710B are porous. Plates 1710A, 1710B may have a pore size in the range of approximately 10-1000 µm, and preferably approximately 40-60 µm, and more preferably approximately 50 µm, and may have a porosity in the range of approximately 30% to 90%, and preferably at least 40%, and more preferably approximately 70% such that when the structure is placed against a bone, such porosity allows for bone ingrowth into the pores of the structure to further secure plates 1710A, 1710B against the bone for long-term bone fixation. The porosity of plates 1710A, 1710B preferably may be defined by porous geometries or may be random as desired, as described with respect to porous structure 1630. Plates 1710A, 1710B may have a varying porosity, which may be a gradient porosity, throughout a portion or parts of the structure. Plates 1710A, 1710B may be porous throughout their entireties, although in alternative arrangements, only a portion of any of the plates of the bone repair device may be porous depending on the needed interface of the plates with bone to provide the appropriate fixation.

As further shown, sutures 1725 are directly attached to each of plates 1710A, 1710B. As in this example, sutures 1725 may be embedded into plates 1710A, 1710B and may hang loosely from the plates for attachment to soft tissue as desired. As further shown, sutures 1725 may be symmetrically placed about partial loop 1720, although in alternative arrangements, such sutures may be attached at any location of plates 1710A, 1710B that allows access to such sutures upon proper placement of plates 1710A, 1710B.

Figure 4A:
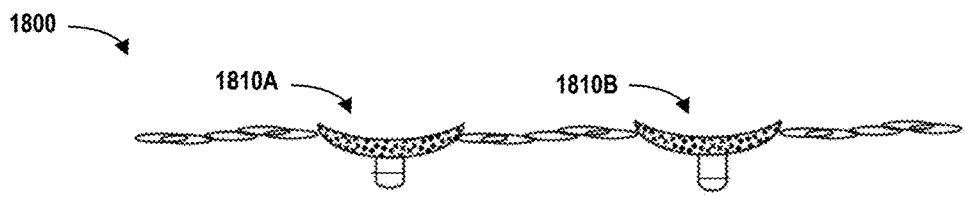
Figure 4B:
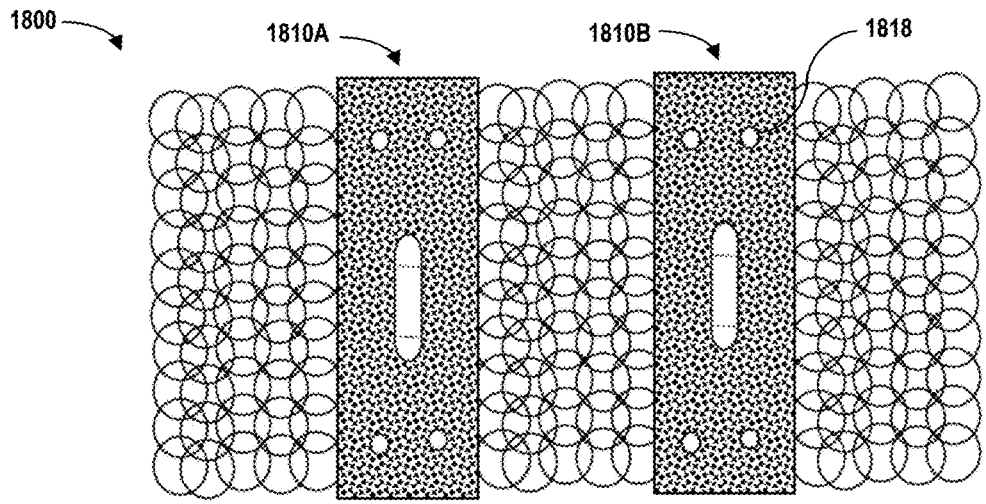

In the example shown in FIGS. 4A and 4B, bone repair device 1800 is the same or substantially similar to bone repair device 1700 with the exception that bone repair device 1800 includes a plurality of plates 1810A, 1810B in place of the plurality of plates 1710A, 1710B. Plates 1810A, 1810B are the same or substantially similar to plates 1710A, 1710B with the exception that plates 1810A, 1810B include holes 1818, which may be at least partially threaded or which may not be threaded, extending through a thickness of the plates in place of the sutures attached to the plates as in plates 1710A, 1710B. In this manner, screws or other fasteners, which may be suture anchors, may be inserted into the holes. In alternative arrangements, holes 1818 may be blind holes. Fasteners attached to plates 1810A, 1810B may be threaded to both the plates and to bone to further secure the plates. Suture anchors (not shown), which may or may not be used to attach plates 1810A, 1810B, may be attached by way of suture to soft tissue.

Figures 5A, 5B:
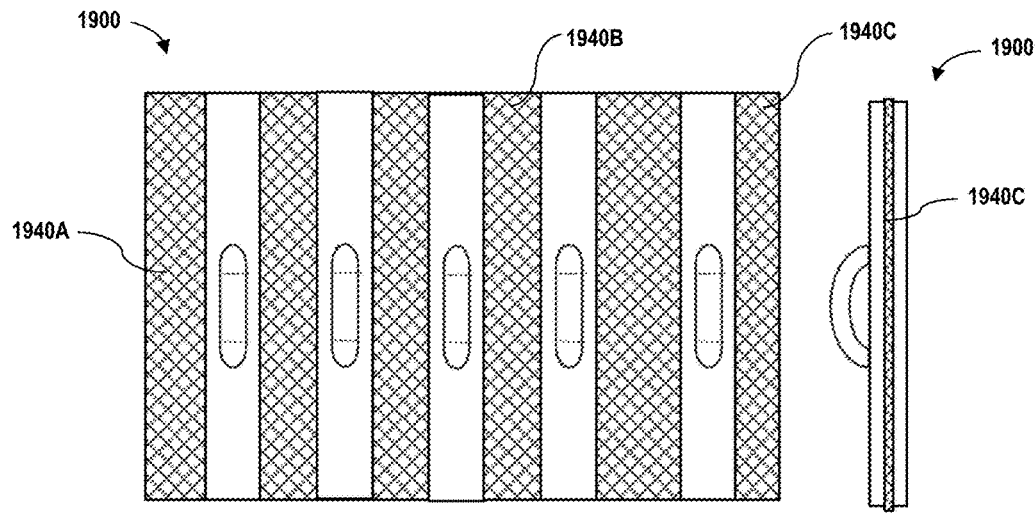

As shown in FIGS. 5A and 5B, bone repair device 1900 is the same or substantially similar to bone repair device 1500 with the exception that bone repair device 1900 includes flexible structures 1940A-1940C in place of flexible structures 1540A-1540C. Flexible structures 1940A-1940C are in the form of meshes, which preferably may be in the form of mesh sheet 150 described further herein. Although flexible structures 1940A-1940C are flexible, such structures are more rigid than flexible structures 1540A-1540C such that flexible structures 1940A-1940C generally require an applied force, such as may be applied by a human hand, to bend such structures in contrast to flexible structures 1540A-1540C that generally may bend into the contour of surfaces against which such structures are placed.

Figure 6A:
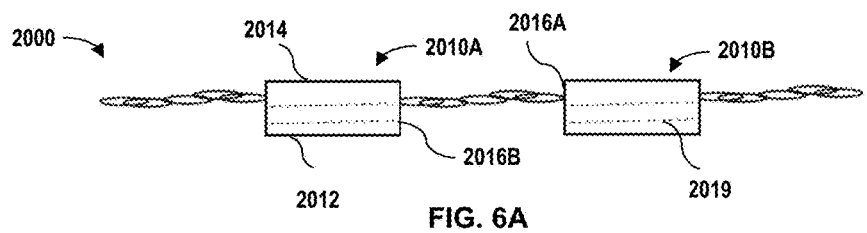
Figures 6B, 6C:
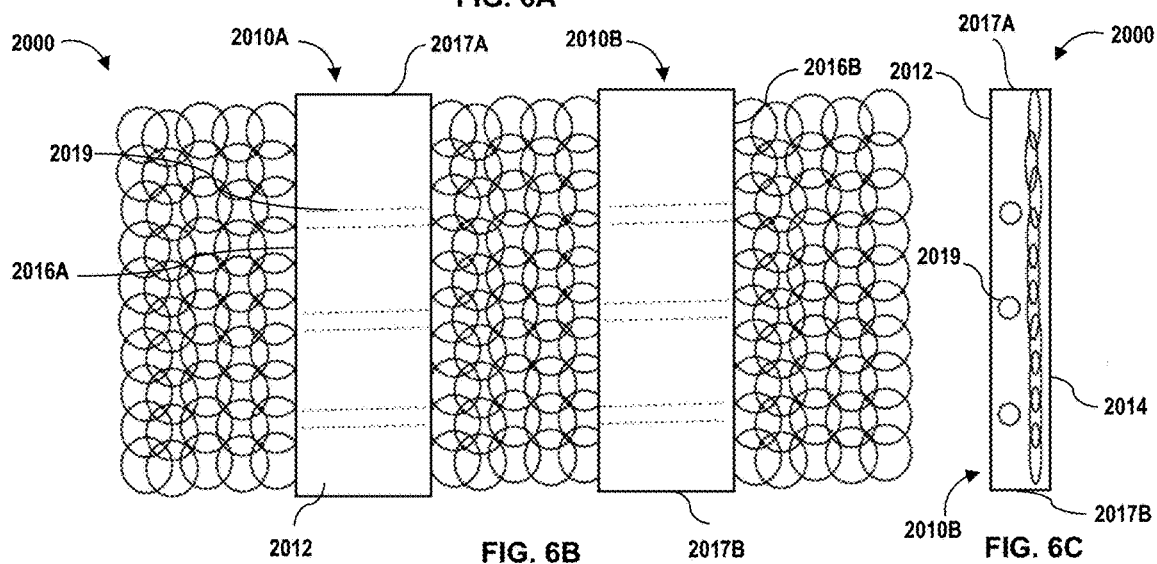

Referring now to FIGS. 6A-6C, bone repair device 2000 is the same or substantially similar to bone repair device 1500 with the exception that bone repair device 2000 includes a plurality of plates 2010A, 2010B in place of the plurality of plates 1510A, 1510B. Plates 2010A, 2010B are the same or substantially similar to plates 1510A, 1510B with the exception that plates 2010A, 2010B include flat top surface 2012 and opposing flat bottom surface 2014 attached to and spaced from the top surface by the plurality of sides 2016A, 2016B, 2017A, 2017B in place of top surface 1512, bottom surface 1514, and the plurality of sides 1516A, 1516B, 1517A, 1517B, respectively, and further include a plurality of holes 2019 acting as channels extending through a thickness of the plates in which longitudinal axes defined by each of holes 2019 extends across a width of the plates, i.e., in a direction transverse to and in this example perpendicular to the direction longitudinal axes defined by holes 1618 described previously herein extend relative to plates 1610A, 1610B. As shown in this example, flexible structures 2040A-2040C, which may be the same or substantially similar to flexible structures 1540A-1540C, respectively, may be offset from the plurality of holes 2019. In this manner, one or more cables, which preferably may be a cerclage wire, may be passed through any of the plurality of holes 2019 in the same manner that such cables may be passed between partial loop 1520 and top surface 1512 plates 1510A, 1510B.

In the example shown in FIGS. 7A and 7B, bone repair device 2100 is the same or substantially similar to bone repair device 2000 with the exception that bone repair device 2100 includes a plurality of plates 2110A, 2110B in place of the plurality of plates 2010A, 2010B. Plates 2110A, 2110B are the same or substantially similar to plates 2010A, 2010B with the exception that plates 2110A, 2110B include a plurality of recesses 2119 acting as channels in place of the plurality of holes 2019. Recesses 2119 operate in the same manner as holes 2019 as they are essentially the same as holes 2019 but offset toward flat top surface 2112 such that the recesses are truncated holes that define an opening and expose the holes. In this manner, each recess 2119 allows an end of a cable to be inserted into either of sides 2116A, 2116B (and, in alternative arrangements in which the recesses extend in a transverse direction, sides 2117A, 2117B) and a section of the cable to be inserted into top surface 2112 of the plate 2110A, 2110B having the recess. As in this example, the opening within top surface 2112 defined by each recess 2119 may be less than a diameter of the cable at rest such that the cable must be compressed to be inserted into the opening. In this manner, the cable remains within recess 2119, i.e., does not fall out of the recess, without a sufficient applied force.

In the example of FIGS. 8A and 8B, bone repair device 2200 is the same or substantially similar to bone repair device 2100 with the exception that bone repair device 2200 includes a plurality of plates 2210A, 2210B in place of the plurality of plates 2110A, 2110B. Plates 2210A, 2210B are the same or substantially similar to plates 2110A, 2110B with the exception that plate 2210A includes a set of recesses 2219A acting as channels and plate 2210B includes a set of recesses 2219B acting as channels in place of the plurality of recesses 2119 of plates 2110A, 2110B. Recesses 2219A, 2219B each include two linear portions offset from each other and a respective circular portion 2220A, 2220B, in the form of a "roundabout" connecting the two linear portions. In this manner, a cable may be inserted into one of the linear portions of either one or both of recesses 2219A, 2219B, may be wrapped around the corresponding circular portion or portions 2220A, 2220B, and may exit out of the corresponding other linear portion of either one or both of the recesses of plates 2210A, 2210B, as the case may be.

As shown in FIGS. 9A and 9B, bone repair device 2300 is the same or substantially similar to bone repair device 2100 with the exception that bone repair device 2300 includes a plurality of plates 2310A, 2310B in place of the plurality of plates 2110A, 2110B. Plates 2310A, 2310B are the same or substantially similar to plates 2110A, 2110B with the exception that plate 2310A includes a plurality of recesses 2319A, 2319B acting as channels and plate 2310B includes a plurality of recesses 2320A, 2320B acting as channels in place of the plurality of recesses 2119 of plates 2110A, 2110B. As shown, each of recesses 2319A, 2319B extend across a width of plate 2310A such that recesses 2319A, 2319B intersect opposing sides 2316A, 2316B of plate 2310A at an oblique angle, and likewise, each of recesses 2320A, 2320B extend across a width of plate 2310B such that recesses 2320A, 2320B intersect opposing sides 2316C, 2316D of plate 2310B at an oblique angle. As in the example shown, recess 2319A of plate 2310A and recess 2320A of plate 2310B may extend at angles such that a cable may be inserted through both of recesses 2319A, 2320A, and likewise, recess 2319B of plate 2310A and recess 2320B of plate 2310B may extend at angles such that a cable, which may be the same or a different cable than the cable inserted through recesses 2319A, 2320A, may be inserted through both of recesses 2319B, 2320B. In alternative arrangements, the angles at which any combination of these recesses extend may be the same angle to better facilitate cable insertion.

Referring now to FIGS. 10A-10C, bone repair device 2400 is the same or substantially similar to bone repair device 1500 with the exception that bone repair device 2400 includes a set of separated plates 2410A, 2410B in place of plate 1510A, a set of separated plates 2410C, 2410D in place of the plurality of plates 1510A, 1510B, and flexible structure 2440 in place of the set of flexible structures 1540A-1540C. Each of separated plates 2410A-2410D are the same or substantially similar to plates 1510A, 1510B with the exception that each of separated plates 2410A-2410D include only a single partial loop 2420 such that each of separated plates 2410A-2410D may be shorter than plates

1510A, 1510B. Flexible structure 2440 extends between separated plates 2410A, 2410B and between separated plates 2410C and 2410 such that the flexible structure is continuous. In this manner, bone repair device 2400 allows for relatively greater flexibility and porosity than bone repair device 1500.

Figure 11A:
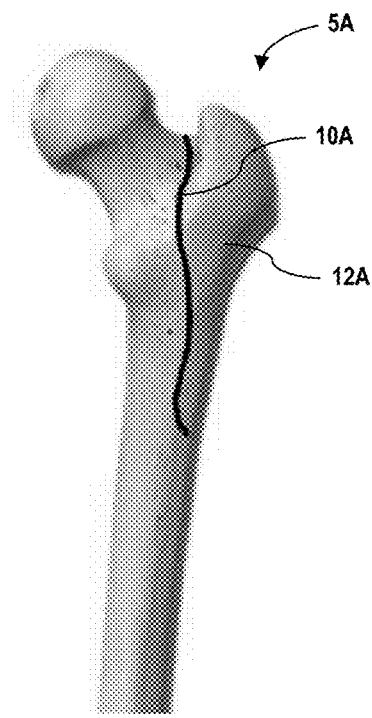
FIG. 11A is a perspective view of a fractured trochanter.
Figure 11B:
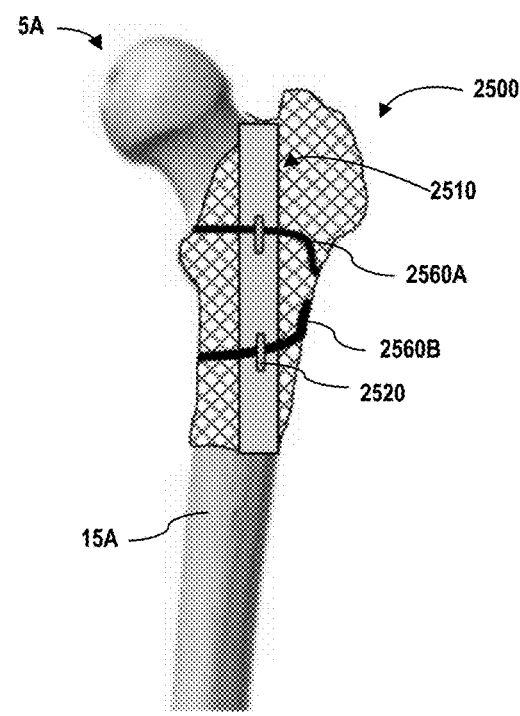
FIG. 11B is a perspective view of a bone repair device placed onto the fractured trochanter of FIG. 11A in accordance with an embodiment.

Referring now to FIGS. 11A and 11B, in repairing fracture 10A across trochanter 12A of femur 5A, bone repair device 2500 is placed around the trochanter such that an edge of the bone repair device is adjacent to neck 14A of the femur and such that the bone repair device extends to body, i.e., shaft, 15A of the femur. Plate 2510, which is substantially similar to plates 1510A, 1510B except that plate 2510 includes only two partial loops 2520, is placed along the trochanter. Preferably, the plate is placed such that a longitudinal axis of the plate extends at an oblique angle to the fracture, as in the example shown, and more preferably the plate is placed such that the longitudinal axis of the plate extends orthogonally to the fracture. Separate cables 2560A, 2560B, each of which as in this example may be a cerclage wire, are passed between partial loops 2520 and the top surface of plate 2510, and wrapped around flexible structure 2540 of bone repair device 2500 and the trochanter to secure the bone repair device to the trochanter. In this manner, bone repair device 2500 facilitates bone ingrowth into flexible structure 2540 and eventually a reduction of fracture 10A. In some alternative arrangements, separate cables 2560A, 2560B may be replaced with a single cable that is wrapped around flexible structure 2540 and the trochanter to secure the bone repair device.

Figure 12A:
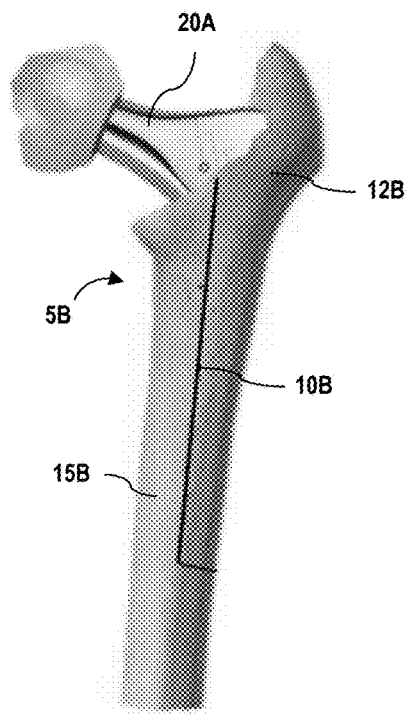
FIG. 12A is a perspective view of a trochanter after an ETO procedure as the trochanter may appear during a revision surgery.
Figure 12B:
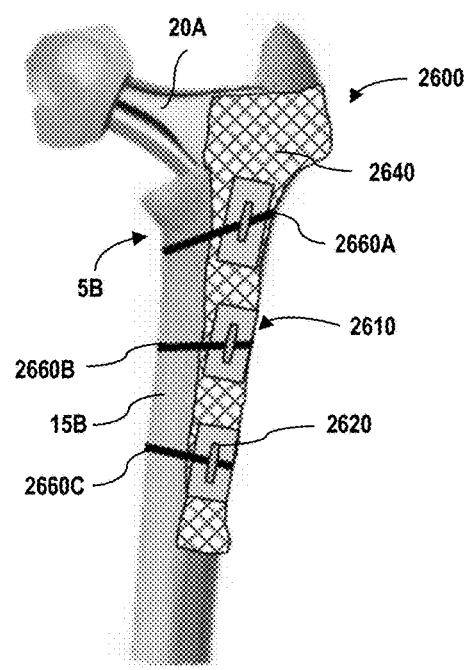
FIG. 12B is a perspective view of a bone repair device placed onto the trochanter of FIG. 12A after the ETO procedure in accordance with an embodiment.

In another example, as shown in FIG. 12A, trochanter 12B may be resected along resection 10B during an ETO procedure after an implant revision surgery as known to those of ordinary skill in the art. With reference to FIG. 12B, in repairing trochanter 12B following the ETO procedure, bone repair device 2600 is placed around the trochanter such that an edge of the bone repair device overlaps hip implant 20A inserted into femur 5B and such that the bone repair device extends to body 15B of the femur. Plates 2610, which are substantially similar to plates 2410A-2410D and which are attached to each other by and separated from each other by flexible structure 2640, are placed along trochanter 12B. Separate cables 2660A, 2660B, 2660C, each of which as in this example may be a cerclage wire, are passed as shown, or in some alternative arrangements a single cable is passed, between partial loops 2620 and the top surface of each plate 2610, and wrapped around flexible structure 2640 of bone repair device 2600 to secure the bone repair device to trochanter 12B. In this manner, bone repair device 2600 facilitates bone ingrowth into flexible structure 2640 and eventually a repair of the resected trochanter.

Referring now to FIG. 13A, trochanter 12C of femur 5C has been weakened, which may be due to stress during insertion of hip implant 20B into the femur or due to bone remodeling over time. With reference to FIG. 13B, in repairing trochanter 12C, bone repair device 2700 is placed around the trochanter such that an edge of the bone repair device overlaps hip implant 20B inserted into femur 5C and such that the bone repair device extends to body 15C of the femur. Plates 2710, which are substantially similar to plates 2010A, 2010B and which are attached to each other by and separated from each other by flexible structure 2740, are placed along trochanter 12C. Separate cables 2760A, 2760B, each of which as in this example may be a cerclage wire, are passed as shown, or in some alternative arrangements a single cable is passed through respective channels extending through each of plates 2710 and wrapped around flexible structure 2740 of bone repair device 2700 to secure the bone repair device to trochanter 12C. In this manner, bone repair device 2700 facilitates bone ingrowth into flexible structure 2640 and eventually a repair of the resected trochanter.

Figure 14:
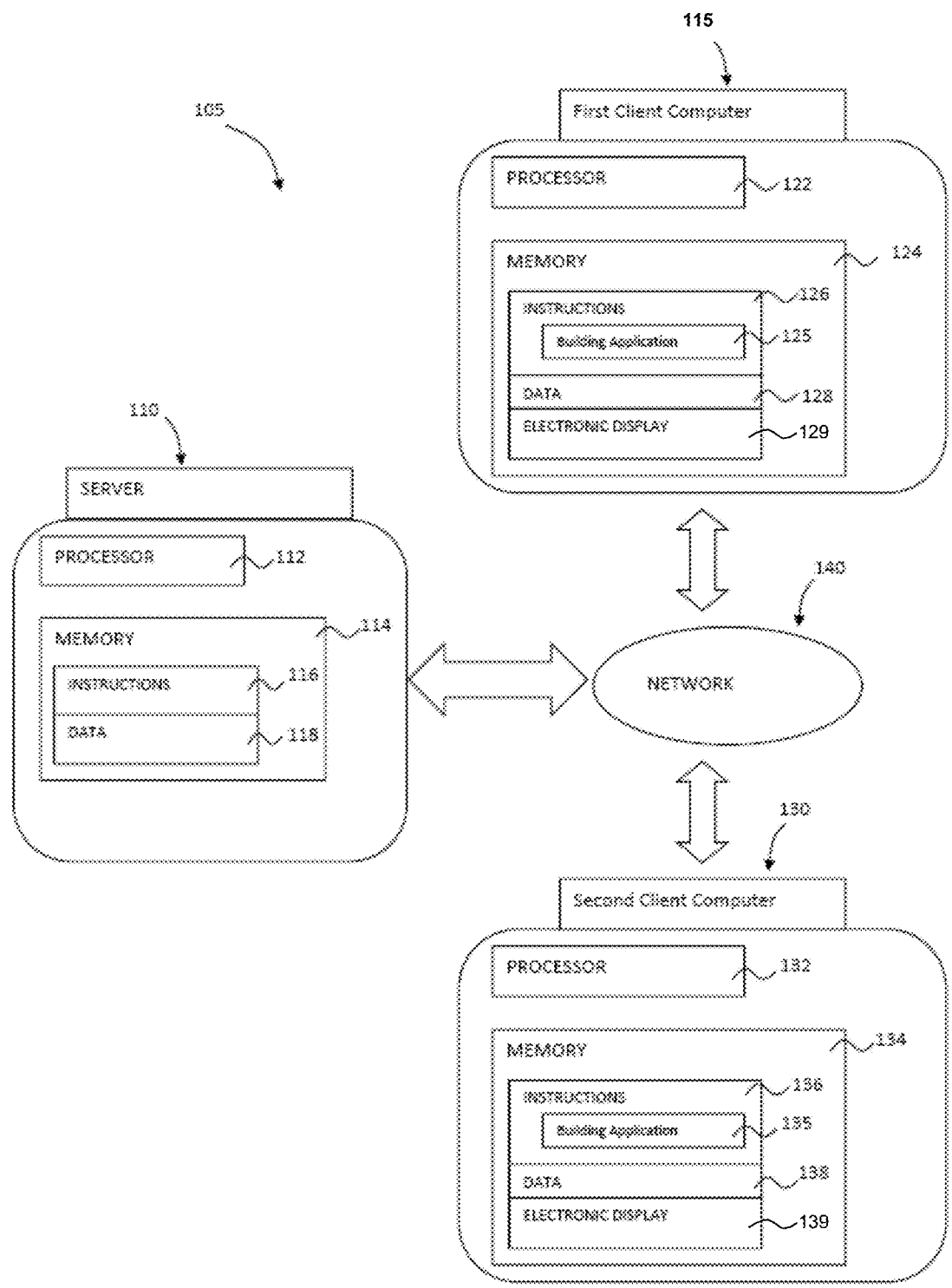
FIG. 14 is a functional diagram of a system in accordance with an embodiment.

Referring now FIG. 14, system 105 may be used, among other functions, to generate, store and share three-dimensional models of structures as part of the preparation of a bone repair device, such as any of the bone repair devices described previously herein. System 105 may include at least one server computer 110, first client computer 115, and in some instances, at least second client computer 130. These computers may send and receive information via network 140. For example, a first user may generate a model at first client device 115. The model may then be uploaded to server 110 and distributed via network 140 to second client computer 130 for viewing and modification by a second user, who or which may be the first user.

Figure 15:
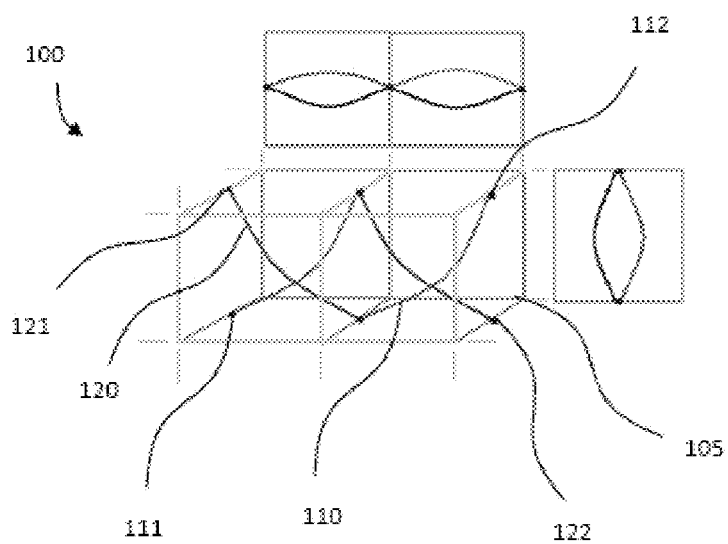
FIGS. 15-17B are various views of three-dimensional model representations of unit cells having wireframes located therein in accordance with other embodiments.

Network 140, and intervening communication points, may comprise various configurations and protocols including the Internet, World Wide Web, intranets, virtual private networks, wide area networks, local networks, private networks using communication protocols proprietary to one or more companies, Ethernet, WiFi and HTTP, and various combinations of the foregoing. Such communication may be facilitated by any device capable of transmitting data to and from other computers, such as modems (e.g., dial-up, cable or fiber optic) and wireless interfaces. Although only a few devices are depicted in FIG. 15, a system may include a large number of connected computers, with each different computer being at a different communication point of the network.

Each of computers 110, 115, 130 may include a processor and memory. For example, server 110 may include memory 114 which stores information accessible by processor 112, computer 115 may include memory 124 which stores information accessible by processor 122, and computer 130 may include memory 134 which stores information accessible by processor 132.

Each of processors 112, 122, 132 may be any conventional processor, such as commercially available CPUs. Alternatively, the processors may be dedicated controllers such as an ASIC, FPGA, or other hardware-based processor. Although shown in FIG. 14 as being within the same block, the processor and memory may actually comprise multiple processors and memories that may or may not be stored within the same physical housing. For example, memories may be a hard drive or other storage media located in a server farm of a network data center. Accordingly, references to a processor, memory, or computer will be understood to include references to a collection of processors, memories, or computers that may or may not operate in parallel.

The memories may include first part storing applications or instructions 116, 126, 136 that may be executed by the respective processor. Instructions 116, 126, 136 may be any set of instructions to be executed directly (such as machine code) or indirectly (such as scripts) by the processor. In that regard, the terms "applications," "instructions," "steps" and "programs" may be used interchangeably herein.

The memories may also include second part storing data 118, 128, 138 that may be retrieved, stored or modified in accordance with the respective instructions. The memory may include any type capable of storing information accessible by the processor, such as a hard-drive, memory card, ROM, RAM, DVD, CD-ROM, write-capable, and read-only memories or various combinations of the foregoing, where applications 116 and data 118 are stored on the same or different types of media.

In addition to a processor, memory and instructions, client computers 115, 130 may have all of the components used in connection with a personal computer. For example, the client computers may include electronic display 129, 139 (e.g., a monitor having a screen, a touch-screen, a projector, a television, a computer printer or any other electrical device that is operable to display information), one or more user inputs (e.g., a mouse, keyboard, touch screen and/or microphone), speakers, and all of the components used for connecting these elements to one another.

Instructions 126, 136 of first and second client devices 115, 130 may include building applications 125, 135. For example, the building applications may be used by a user to create three-dimensional structures, such as those described further herein. The building applications may be associated with a graphical user interface for displaying on a client device in order to allow the user to utilize the functions of the building applications.

A building application may be a computer-aided design (CAD) 3-D modeling program or equivalent as known in the art. Available CAD programs capable of generating such a structure include Autodesk® AutoCAD®, Creo® by Parametric Technology Corporation (formerly Pro/Engineer), Siemens PLM Software NX™ (formerly Unigraphics NX), SOLIDWORKS® by SolidWorks Corporation, and CATIA® by Dassault Systemes. Such structures may be those described in the '901 Patent.

Data 118, 128, 138 need not be limited by any particular data structure. For example, the data may be stored in computer registers, in a relational database as a table having a plurality of different fields and records, or XML documents. The data also may be formatted into any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations) or information that is used by a function to calculate the relevant data. For example, data 128 of first client device 115 may include information used by building application 125 to create three-dimensional models.

In addition to the operations described above and illustrated in the figures, various other operations will now be described. It should be understood that the following operations do not have to be performed in the precise order described below. Rather, various steps may be handled in a different order or simultaneously. Steps also may be omitted or added unless otherwise stated herein.

An overall three-dimensional representation of a component, such as any of the bone repair devices described previously herein, may first be generated by preparing a CAD model. This overall CAD model may be comprised of one or more distinct CAD volumes that are intended to be manufactured as either solid or porous physical structures, i.e., constructs that may be separated from each other.

Solid CAD volumes, which correspond to manufactured solid physical structures, can be sliced into layers of a predetermined thickness ready for hatching, re-merging with one or more corresponding porous volumes (post-lattice generation), and subsequent manufacture.

Porous CAD volumes, such as porous CAD volume 100 shown in the example of FIG. 15 and which correspond to manufactured porous geometries, can be processed using bespoke software. As in the example of FIG. 15, an example of a porous geometry is made up of one or more segments 110, 120 organized within tessellated unit cells 105. Many designs are possible for a porous geometry which allows the porous geometry to impart various strength, surface, and/or other characteristics into the porous CAD volume. For example, porous geometries can be used to control the shape, type, degree, density, and size of porosity within the structure. Such porous geometry shapes can be dodecahedral, octahedral, tetrahedral (diamond), as well as other various shapes.

As further shown in FIG. 15, and as more fully described in U.S. Patent Application Publication No. 2017/0165790 A1 and U.S. Patent Application Publication No. 2018/0361510 A1, the disclosures of which are hereby incorporated by reference herein, porous CAD volume 100 is formed by a plurality of unit cells 105 which each contain curvilinear segment geometry 110 and curvilinear segment geometry 120. Curvilinear segment geometry 110 within each unit cell 105 extend from an end 111 thereof located at a center of a lower left edge of the unit cell to an end 112 thereof located at a center of an upper right edge of the unit cell, and curvilinear segment geometries 120 within each unit cell 105 extend from an end 121 thereof located at a center of an upper left edge of the unit cell to an end 122 thereof located at a center of a lower right edge of the unit cell.

Unit cells 105 are adjacent to each other such that end 112 of curvilinear segment geometry 110 within one unit cell 105 abuts, and indeed is the same as, end 121 of curvilinear segment geometry 120 within adjacent unit cell 105 and such that end 122 of curvilinear segment geometry 120 within one unit cell 105 abuts, and is the same as, end 111 of curvilinear segment geometry 110 within adjacent unit cell 105. As shown, curvilinear segment geometry 110 within each unit cell 105 curves around curvilinear segment geometry 120 within the same unit cell. In this manner, a connected pair of curvilinear segment geometry 110 and curvilinear segment geometry 120 within adjacent unit cells 105 overlaps the other connected pair of curvilinear segment geometry 110 and curvilinear segment geometry 120 within the same adjacent unit cells.

Figure 16:
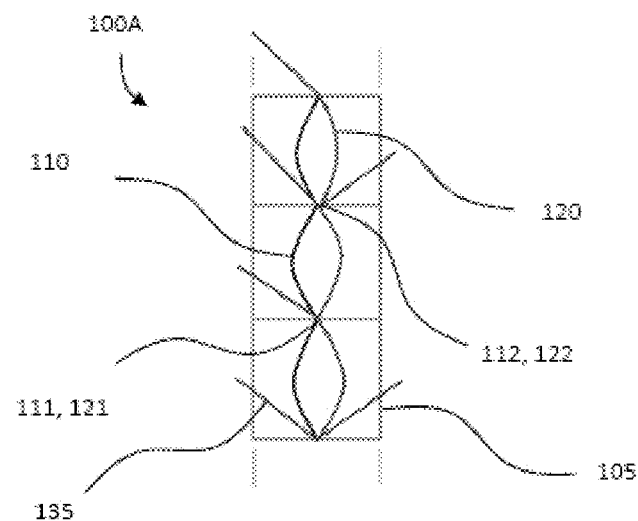

As shown in FIG. 16, porous CAD volume 100A includes unit cells 105 formed adjacent to other unit cells 105 such that ends of curvilinear segment geometries 110, 120 of one unit cell abut an end of the other curvilinear segment geometry of respective curvilinear segment geometries 110, 120 of the adjacent unit cell. As further shown, a plurality of barb geometries 135 extend from various ends 111, 112 of curvilinear segment geometries 110 and ends 121, 122 of curvilinear segment geometries 120 such that barb geometries 135 extend transversely across the curvilinear segment geometries 110, 120 corresponding to the respective ends. In this manner, a plurality of unit cells 105 may be tessellated to form the porous CAD volume 100A.

When used for medical implants, barb geometries, such as barb geometries 135, may correspond to physical barbs that encourage directional fixation of an implant. In such applications, the barbs may vary in spacing and length. Such barbs may be but are not limited to being on the order of 0.6-1.2 mm in length. Any directional barb hairs, branches, rods, and beads also may be incorporated into a porous mesh structure to encourage directional fixation with bone. As barb geometries, such as barb geometries 135, may be placed at any predetermined or, conversely, at randomly selected positions along segment geometries of a porous CAD volume, barbs corresponding to the barb geometries may be placed at any such corresponding positions on segments corresponding to segment geometries.

Figure 17A:
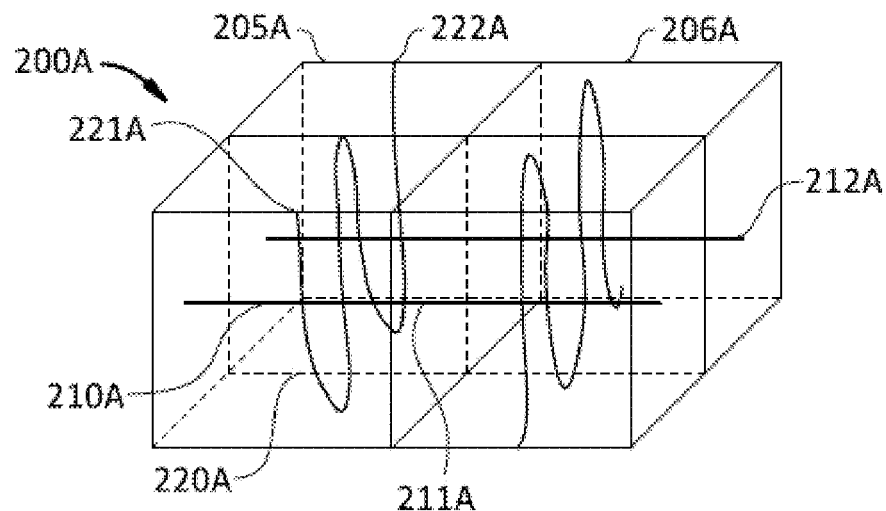

Referring now to FIG. 17A, porous CAD volume 200A is formed by tessellation of a plurality of unit cells 205A, 206A each containing linear segment geometry 210A and curvilinear segment geometry 220A. As in this example, opposing ends 211A, 212A of linear segment geometry 210A within each unit cell 205A, 206A may extend from centers of opposite faces of the unit cell, and curvilinear segment geometry 220A of each unit cell 205A may extend from an end 221A thereof located at a center of an upper front edge of the unit cell, around the linear segment geometry, and to an end 222A thereof located at a center of an upper rear edge of the unit cell. In this manner, segment geometries 210A, 220A form portions of mesh geometry.

A plurality of unit cells 205A and separately a plurality of unit cells 206A may be adjacent to each other such that end 221A of curvilinear segment geometry 210A of one unit cell 205A, 206A abuts end 222A of curvilinear segment geometry 220A of respective adjacent unit cell 205A, 206A. As further shown, the plurality of unit cells 206A may be inverted relative to the plurality of unit cells 205A, and end 211A of linear segment geometry 210A of one unit cell 205A may abut end 212A of linear segment geometry 210A of respective adjacent unit cell 206A. In this manner, curvilinear segment geometries 210A of each of the plurality of unit cells 205A, 206A and the linear geometries 210A of each of the plurality of unit cells 205A, 206A may collectively form a woven mesh geometry. As in the example shown, linear segment geometries 210A of the plurality of unit cells 205A, 206A may all be parallel to each other.

Figure 17B:
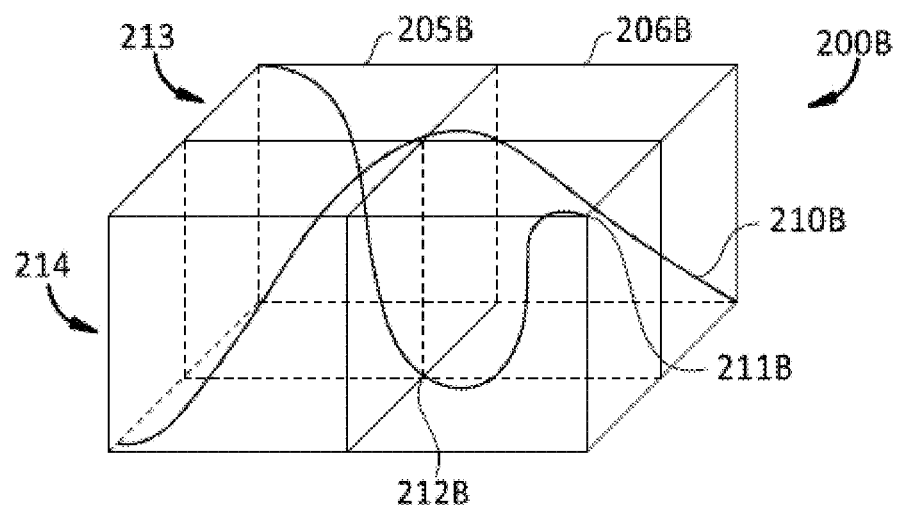

Referring to FIG. 17B, porous CAD volume 200B is formed by tessellation of a plurality of unit cells 205B, 206B each containing curvilinear segment geometry 210B in which curvilinear segment geometry 210B of unit cell 206B is inverted relative to curvilinear segment geometry 210B of unit cell 205B. As in this example, opposing ends 211B, 212B of curvilinear segment geometry 210B of each unit cell 205B, 206B may extend from opposite corners of the respective unit cells. Unit cells 205B may be diagonal from each other such that they share only one common edge, and similarly, unit cells 206B may be diagonal from each other such that they share only one common edge. In this manner, ends 212B of curvilinear segment geometries 210B of each of a first set of unit cells 205B, 206B may abut ends 211B of curvilinear segment geometries 210B of each of a second set of unit cells 205B, 206B located diagonally to the first set of the unit cells. In this manner, a connected pair of curvilinear segment geometry 210B of diagonally located set of unit cells 205B overlaps a connected pair of curvilinear segment geometry 210B of diagonally located set of unit cells 206B to form a mesh geometry. As shown, such mesh geometry may be in the form of a woven mesh.

A larger mesh geometry may be formed by adding further sets of the four unit cells 205B, 206B to each of the four sets of two side faces 213, 214 of adjoining unit cells 205B, 206B, i.e., to the side faces 213, 214 around the circumference of the four cubes shown in the illustration of FIG. 17B. In alternative arrangements, the mesh geometry defined by the four curvilinear segments 210B of the four unit cells 205B, 206B shown in FIG. 17B may be arranged in a single unit cell, which may be tessellated to form a porous CAD volume.

Other variations of unit cells 105 and 205, 206 in which at least one segment geometry defining the unit cell is curved or includes angled portions, which may be in the shape of a "V," "W" or other combination of linear portions, such that the segment geometry curves or wraps around another segment geometry of the unit cell are within the scope of the present technology. Such variations could also be used to form porous CAD volumes. In other arrangements, a CAD model may be generated without forming unit cells and thus without tessellation of features within the unit cells. Such CAD models created without tessellated unit cells may be in the form of a woven mesh, i.e., cross-hatch, geometry with overlapping and underlapping strips, i.e., ribbons. In some alternative arrangements, woven mesh geometries may have a plurality of adjacent segment geometries or set of segment geometries that overlap and underlap the same transverse corresponding segment geometries or set of segment geometries, e.g., in the form of a "double weave." In other variations of forming mesh geometries, the ends of the segment may be at any location within a unit cell so long as the segment geometries of each unit cell, alone or in combination with segment geometries of adjacent unit cells overlap and underlap segment geometries within the same unit cell or within adjacent unit cells, i.e., in a manner similar to the overlapping and underlapping of the segment geometries shown in FIGS. 17A and 17B. For example, ends may be but are not limited to being at corners of unit cells, centers of edges of unit cells, and the centers of faces of unit cells. In some arrangements, a percentage of the junctions where segment geometries of a porous CAD volume overlap each other may be fused together. When fusion of such junctions is unevenly distributed, anisotropy in a physical mesh structure corresponding to a porous CAD volume may be created.

Figure 18:
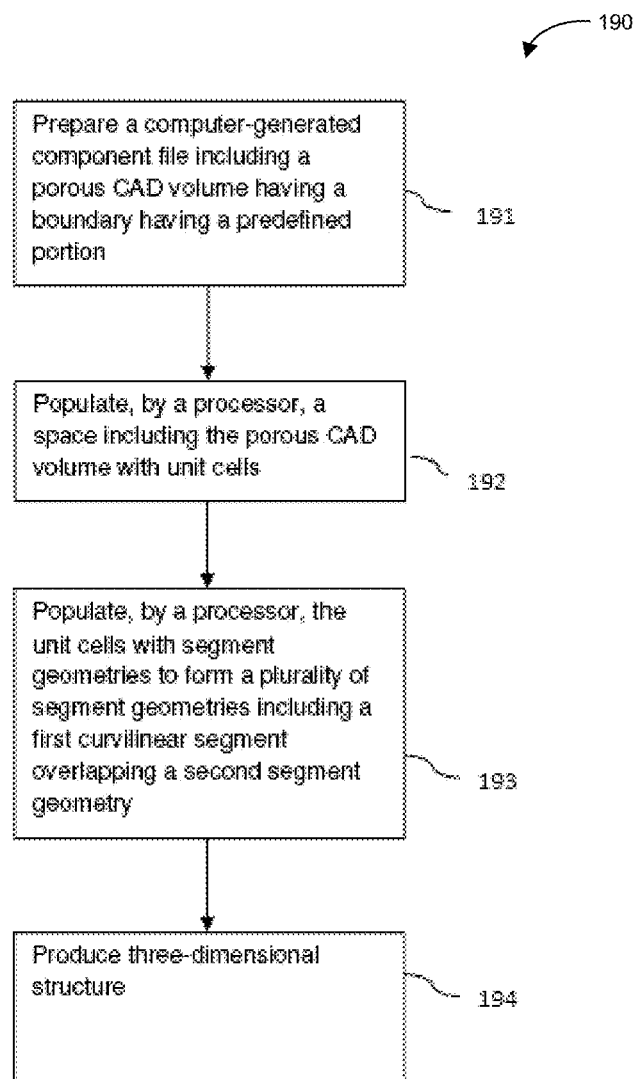
FIG. 18 is a process flow diagram in accordance with another embodiment.

Referring to FIG. 18, in process 190 for preparing a porous CAD volume of segment geometries, such as a CAD volume of a flexible structure of a bone repair device, a computer-generated component file is prepared at block 191. The component file includes a porous CAD volume with a boundary having at least one predefined portion. At block 192, a space that includes the porous CAD volume is populated, by a processor, with unit cells. Such a space may be defined by sets of coordinates, such as Cartesian, polar, or spherical coordinates. At block 193, the unit cells are populated with one or more segment geometries to form a plurality of segment geometries. As further shown at block 193, a first curvilinear segment geometry of the plurality of segment geometries overlaps a second segment geometry of the plurality of segment geometries and underlaps a third segment geometry of the plurality of segment geometries. In this manner, a computer-generated model of a three-dimensional structure, such as a computer-generated model corresponding to a CAD volume of a flexible structure of a bone repair device, constructed of segment geometries is prepared.

The above-described model geometries can be visualized in a number of ways, including but not limited to by voxelating the sliced output files from bespoke software that is being applied in an ALM machine. Utilizing developed algorithms and the output files, the data may be fed into a commercial software package, e.g., MATLAB® by MathWorks, Inc., and the images produced can be interpreted. At optional block 194, a tangible three-dimensional structure having a shape corresponding to the computer-generated model may be produced. The shape of the three-dimensional structure may be in the form of a mesh structure. Such a mesh structure may be formed in conjunction with a solid structure to form a bone repair device, such as any bone repair device described previously herein.

The approaches for generating the three-dimensional models described herein may be used for building various tangible structures and surfaces, specifically structures and surfaces for medical implants. Upon completion of a CAD model including the porous geometries and any solid geometries that may be connected to the porous geometries, an intended physical structure, such as any bone repair device described previously herein, may be formed directly onto a substrate using a layered additive manufacturing process, including but not limited to electron beam melting (EBM), selective laser sintering (SLS), selective laser melting (SLM), and blown powder fusion for use with metal powders. Techniques such as but not limited to SLS, three-dimensional inkjet printing (3DP), stereolithography (SLA), and fused filament fabrication (FFF) may be used with polymer powders or strands to produce plastic constructs. Cellular scaffolds may be formed using bioplotters or 3DP. Although a brief summary follows, many details of a process of melting powdered metal are given in the '332 Publication and '901 Patent. In an example of constructing a tangible structure from a model build geometry using metal powder, a layer of metal powder may be deposited onto a substrate. The substrate may be a work platform, a solid base, or a core, with the base or core being provided to possibly be an integral part of the finished product.

The metal powder may be but is not limited to being made from any combination of titanium, a titanium alloy, stainless steel, magnesium, a magnesium alloy, cobalt, a cobalt alloy including a cobalt chrome alloy, nickel, a nickel alloy including a nickel titanium alloy such as the super elastic material nitinol, platinum, silver which may provide antimicrobial properties, tantalum, niobium, and other super elastic materials such as copper-aluminum alloys. In some embodiments, individual layers of metal may be scanned using a directed high energy beam, such as a continuous or pulsed laser or e-beam system to selectively melt the powder, i.e., melt the powder in predetermined locations. Each layer, or portion of a layer, is scanned to create a plurality of predetermined porous or mesh physical constructs, and when necessary predetermined solid constructs, by point exposure to the energized beam. This leads to the production of linear, curvilinear, or other shaped struts that correspond to the segments described previously herein and eventually to a porous or mesh physical construct, as will be described below. Successive layers are deposited onto previous layers and also are scanned. The scanning and depositing of successive layers continues the building process of the predetermined porous geometries. As disclosed herein, continuing the building process refers not only to a continuation of a porous or mesh physical construct from a previous layer but also a beginning of a new porous or mesh physical construct as well as the completion of the current porous or mesh physical construct.

In alternative arrangements, non-metallic materials may be used in such ALM processes. These materials may include implantable plastics including but not limited to any one or any combination of wax, polyethylene (PE) and variations thereof, polyetheretherketone (PEEK), polyetherketone (PEK), acrylonitrile butadiene styrene (ABS), silicone, and cross-linked polymers; bioabsorbable glass, ceramics, and biological active materials such as collagen/cell matrices. Composites of any one or any combination of these materials or the metals described previously herein may be made as a combination with any one or any combination of bone cement, bone, soft tissue, and cellular matrices and tissue cells.

A component structure or sub-structure thereof produced by the approaches herein may be porous and if desired, the pores can be interconnecting to provide an interconnected porosity. In some embodiments, the amount and location of porosity may be predetermined, and preferably lie in the range 50% to 90% as being suitable when used as a bone ingrowth surface, and 20% to 90% as being suitable for polymer interlock surfaces. This also applies to cases where the outer porous section of a medical device, such as any bone repair device described previously herein, is connected to host bone with bone cement or bone type adhesives for example.

When physical constructs are produced using a laser or electron beam melting process, a prefabricated base or core may act as a substrate for such constructs, e.g., in fabricating porous structure 1630 of each of plates 1610A, 1610B of bone repair device 1600, bottom surface 1614 of the respective plate may act as a substrate. Such bases may be made of any one or any combination of the materials described previously herein for use in the ALM processes. In some instances, such materials may be different than the materials for the successive layers built during the ALM processes. Thus, a mixture of desired mixed materials can be employed. By way of example, porous layers can be built onto an existing article, which itself may be porous or solid and may be made from any one or any combination of cobalt and its alloys including a cobalt chrome alloy, titanium or its alloys, magnesium and its alloys, stainless steel, nickel and its alloys including a nickel titanium alloy such as the super elastic material nitinol, platinum, silver which may provide antimicrobial properties, tantalum niobium, and other super elastic materials such as copper-aluminum alloys. In this example, the existing article may be an orthopaedic implant, such as any bone repair device described previously herein. In such a manner, the approaches described herein may be exploited to produce commercially saleable implants with bone in-growth structures having porous surfaces with a predetermined scaffold structure. The constructed medical implant, which may have porous or other flexible structures that correspond to the mesh geometries described previously herein, may have a porosity and architecture optimized to create very favorable conditions so that bone in-growth takes place in a physiological environment and the overall outcome favors long-term stability.

Because a laser or electron beam melting process may not require subsequent heat treatment or the temperature at which this heat treatment occurs is lower than any critical phase change in the material, the initial mechanical properties of any base metal to which a porous structure is applied may be preserved.

The equipment used for additive layer manufacturing of implants could be one of many currently available, including but not limited to those manufactured by Renishaw, SLM Solutions, Realizer, EOS, Concept Laser, Arcam and the like. The laser or electron beam also may be a custom-produced laboratory device.

Figure 19:
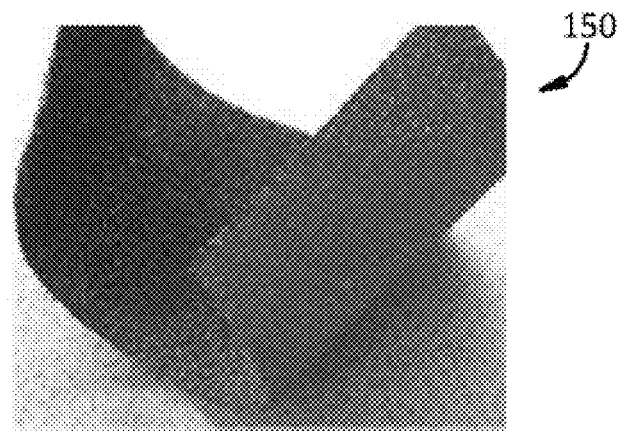
FIG. 19 is an example of a mesh sheet in accordance with another embodiment.

As shown in FIG. 19, mesh sheet 150 was produced by melting successive layers of metal powder. To produce physical constructs of this form, with reference to FIG. 16, spots corresponding to ends 111 of curvilinear segments 110 and ends 122 of curvilinear segments 120 may be formed during production of one layer of an intended physical structure corresponding to porous CAD volume 100A, spots corresponding to ends 121 of curvilinear segments 120 and ends 112 of curvilinear segments 110 may be formed using a high energy beam during production of another layer of the intended physical structure corresponding to porous CAD volume 100A, and spots corresponding to portions of curvilinear segments 110 and portions of curvilinear segments 120 may be formed during production of other layers of the intended physical structure corresponding to porous CAD volume 100A. Such spots may be formed using an SLS or SLM process in which, when a laser is the high energy beam, the powder particles may have a diameter on the order of between and including 5 and 50 µm, and when an electron beam is the high energy beam, the powder particles may have a diameter on the order of between and including 75 and 150 µm. In a similar manner, the geometries of the porous CAD volumes 100, 200A, and 200B as described previously herein may be formed into mesh sheets. Similar constructions may be but are not limited to being formed using any one or any combination of the other additive manufacturing processes discussed previously herein, including 3DP, SLA, FFF, and digital light processing (DLP).

Again referring to FIG. 19, mesh sheet 150 is made of titanium. Due to the rigidity of the material, mesh sheet 150 has been trimmed to size by a pair of scissors, producing little debris relative to other devices that require modification from a Midas Rex or similar device, such as with cone and sleeve augments. Mesh sheet 150 is malleable due to its minimal thickness and thus has been curled into shape. As shown, mesh sheet 150 has also been coated with a PERI-APATITE® hydroxyapatite coating but remains porous to promote bone in-growth. Such a coating may also be applied to flexible structures of bone repair devices such as any of those described previously herein. Although the surfaces of mesh sheet 150 are relatively rough, in alternative arrangements, at least one surface of the mesh sheet may be smooth to prevent irritation to surrounding soft tissues. Such surface may be produced using the techniques taught in the '010 Patent incorporated by reference in its entirety herein.

Figure 20A:
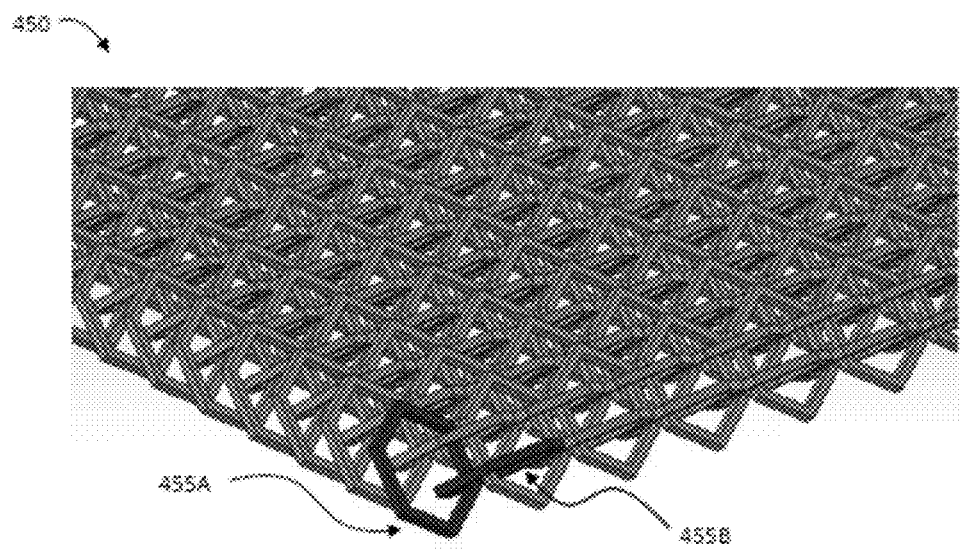
FIGS. 20A and 20B are perspective views of a three-dimensional model representation of a portion of a mesh sheet in accordance with an embodiment.
Figure 20B:
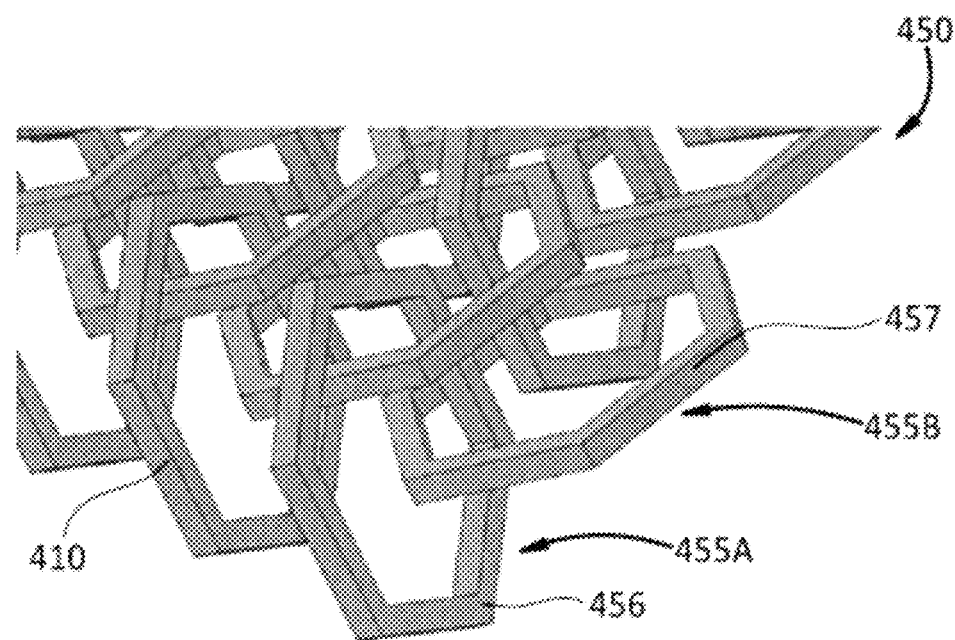

As shown in FIGS. 20A and 20B, a CAD model of mesh sheet geometry 450 includes a set of connected link geometries 455A oriented in a vertical direction and link geometries 455B oriented in a horizontal direction. A "chain link" mesh sheet corresponding to this CAD model including a set of connected links may be formed using any one or any combination of the ALM processes described previously herein in accordance with the present technology.

Still referring again to FIGS. 20A and 20B, as shown, each link geometry 455A, 455B is a substantially planar open hexagon formed of six connected segments 410 which are connected to a plurality of other link geometries 455A, 455B. Each link geometry 455A, 455B has a closed perimeter such that a physically produced link corresponding to this link geometry may not be separated from other links to which the physically produced link is connected without severing one of the connected links. In alternative arrangements, at least some physically produced links may have an opening through their perimeters such that links to which a link is connected may be removed through the opening. In instances in which the opening of an open perimeter is too small, a link having such an opening may be deformable such that the opening may be either one or both of widened and narrowed.

Figure 20C:
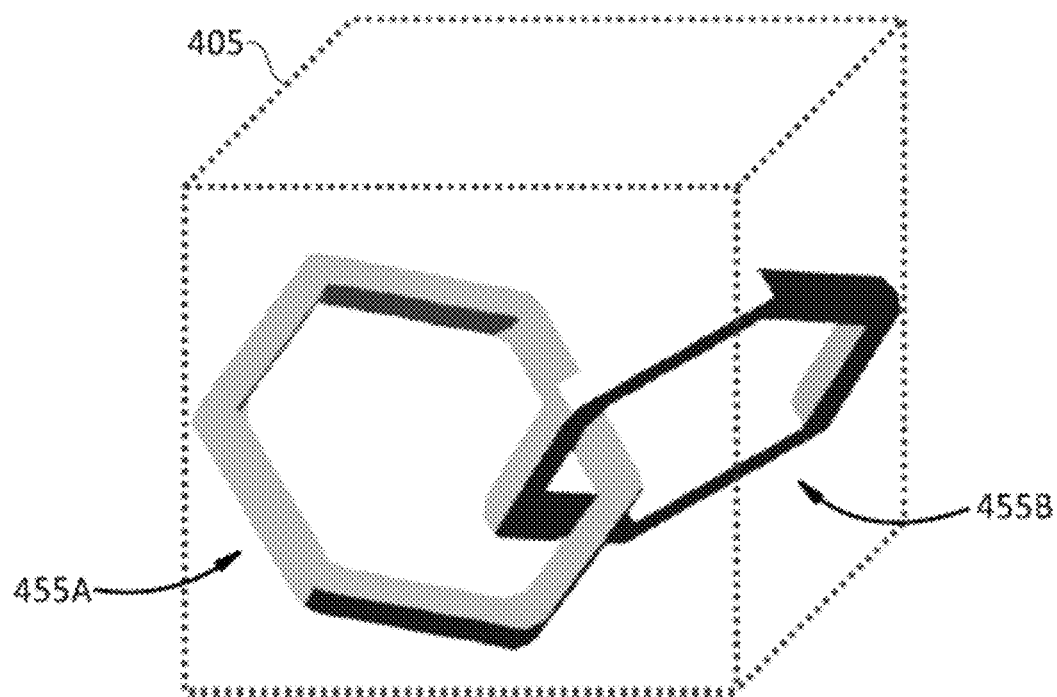
FIG. 20C is a perspective view of a three-dimensional model representation of a unit cell for use in preparing the three-dimensional model representation of the portion of the mesh sheet of FIG. 20A

In one arrangement of forming mesh sheet geometry 450, each link geometry within a CAD model may be modeled individually without the use of tessellated unit cells. In an alternative arrangement as shown in the example of FIG. 20C, unit cell 405 may be tessellated to form mesh sheet geometry 450. As shown, unit cell 405 includes one link geometry 455A interlocked with one link geometry 455B. With reference to FIGS. 9A and 9B, upon tessellation of unit cell 405 to form a porous CAD volume containing mesh sheet geometry 450, each link geometry 455A of one unit cell becomes interlocked with link geometries 455B of adjacent unit cells, and each link geometry 455B of one unit cell becomes interlocked with link geometries 455A of adjacent unit cells. In this manner, in the example of FIGS. 20A and 20B, each link geometry 455A becomes interlocked with four link geometries 455B and each link geometry 455B becomes interlocked with four link geometries 455A.

In the example of FIGS. 20A and 20B, planes defined by a widest dimension of interlocked link geometries 455A, 455B are arranged orthogonally to each other. Interlocked link geometries 455A, 455B are spaced apart a slight distance from each other and have the same size. In alternative arrangements, interlocked link geometries may be set at any non-orthogonal angles to each other, different spacings relative to each other, and different sizes relative to each other. Through these variations, either one or both of the porosity and flexibility of mesh sheets corresponding to modeled mesh sheet geometries may be varied. In some alternative arrangements, unit cells, such as unit cells 405, may be offset by a distance that is different than the spacing between interlocked link geometries of each unit cell to form a non-uniform mesh geometry. In some alternative arrangements, some regions of a mesh geometry may be different in any dimension than other regions of a mesh sheet geometry to form varying porosity, which may be a gradient porosity, within a mesh sheet corresponding to the mesh geometry.

Figure 23A:
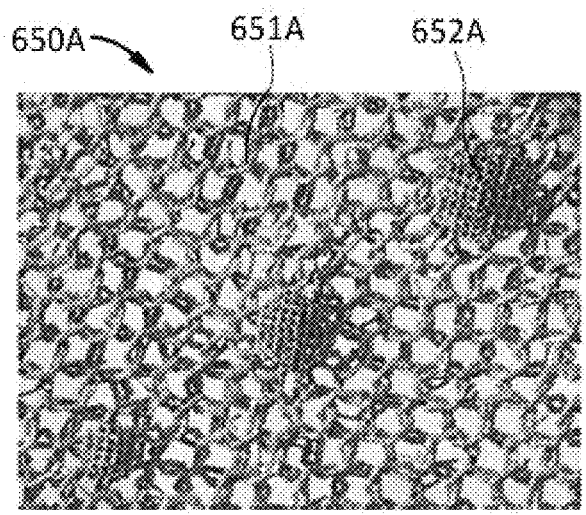
Figure 24A:
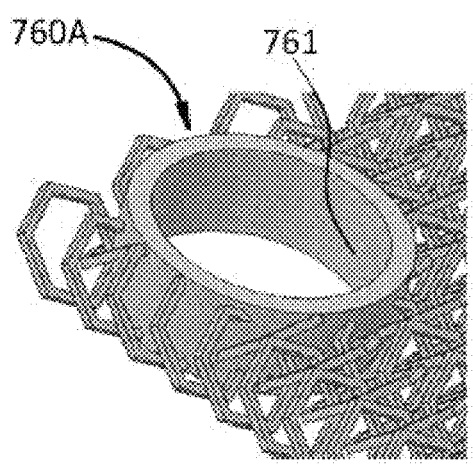
FIG. 24A is a perspective view of a three-dimensional model representation of a portion of a mesh sheet in accordance with an embodiment.
Figure 24B:
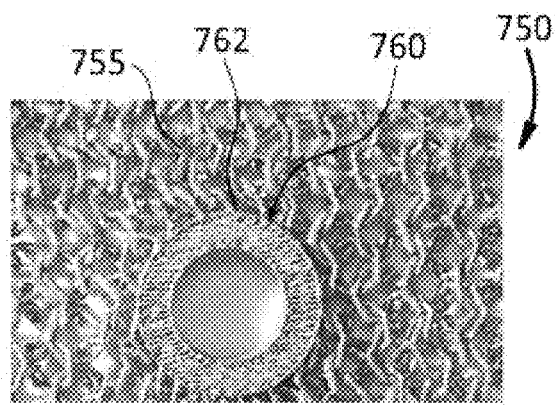
FIG. 24B is a physical construct corresponding to the model mesh sheet of FIG. 24A.

When forming a physical structure corresponding to mesh sheet geometry 450, which may be a mesh sheet or other flexible construct such as those shown in FIGS. 23A and 24B described further herein, a bottom portion of links, such as a bottom portion of a link corresponding to vertices 456 of link geometries 455A, may be formed during preparation of a first layer of the physical structure of the mesh sheet geometry by an ALM device, such as any piece of or any combination of the pieces of equipment discussed previously herein. Successive layers of the physical structure may then be prepared by the ALM device to form complete links corresponding to link geometries 455A, 455B in which, immediately upon completion of the links, links corresponding to link geometries 455A define planes that are aligned vertically, i.e., orthogonally, with respect to a substrate, which may be a build platform or other component structure, on which the physical structure is formed, and links corresponding to link geometries 455B define planes that are aligned horizontally, i.e., parallel, with respect to the substrate. In this manner, and with reference to FIG. 20B, during preparation of the successive layers, only portions of links corresponding to width 457 along opposite sides of the vertically-aligned hexagonal links 455A may be formed in the layers forming links corresponding to horizontally-aligned hexagonal links 455B. In an alternative arrangement, a portion of a plurality of links corresponding to vertices 456 of both link geometries 455A, 455B may be formed during preparation of a first layer of the physical structure of the mesh sheet geometry by an additive manufacturing device. In such an arrangement, successive layers of this physical structure then may be prepared by the ALM device to form the complete links corresponding to link geometries 455A, 455B in which, immediately upon completion of the links, links corresponding to link geometries 455A define planes extending at a nonparallel and a non-orthogonal angle, such as but not limited to an angle of 45 degrees, with respect to the substrate on which the physical structure is formed, and links corresponding to link geometries 455B define planes also extending at a nonparallel and non-orthogonal angle to the substrate, which may be the same angle as the planes defined by the links corresponding to link geometries 455A extend with respect to the substrate, but in an opposite direction as the links corresponding to link geometries 455A extend.

The size of the segments forming the links, which correspond to the segment geometries forming the link geometries, such as link geometries 455A, 455B, the shape of any number of the segments and any number of the links, and thus the sizes of pores defined by the links may be adjusted to suit a particular application of a physical construct such as a mesh sheet. Such variables may be used to control flexibility, range of motion, and strength of an overall construct such as a mesh sheet, as well as to control either one or both of the amount of tissue ingrowth and the egress of contained materials, with pore size and shape optimized to pressurize doughy bone cements or morselized bone graft materials. To achieve these goals, the pore sizes preferably should be greater than 300 µm and strut sizes preferably should be greater than 100 µm. In this manner and depending on material choice, the physical construct may have any one or any combination of a relatively high tensile strength, low flexion and compressive stiffness, variable tensile stiffness, variable stiffness, and ductility.

Any link geometry, and thus the corresponding link in a physical construct, may be but is not limited to being in the shape of a a circle, an ellipse, a polygon such as a hexagon, an octagon, a rectangle, a square, a triangle, and any combination of these shapes. Links may be planar, such as links corresponding to link geometries 455A, 455B in the example of FIGS. 20A and 20B, as well as non-planar, in which links may extend in three dimensions, e.g., a kinked hex or quadrilateral design. In some arrangements, the ratio of strut size to pore size for a given shape of strut corresponding to a segment in a CAD model may be varied to influence flexibility, range of motion, and strength in some or all directions. The ratio of links connected to each link may be adjusted throughout all or a portion of a flexible construct such as a mesh sheet. For example, in a preferred arrangement, a connected link ratio of 4:1 may be used to make a uniform sheet construct. In another example, a connected link ratio of 2:1 may be used to make a chain construct, and in yet another example, odd-numbered connected link ratios may be used to create discontinuous flexible constructs.

Physical constructs formed using link geometries may have a variable porosity, which may be but is not limited to being a graded porosity, by varying either one or both of link size and shape within the same construct to provide for any one or any combination of variable flexibility, variable range of motion, and variable strength throughout the construct. In some arrangements, physical constructs formed using the link geometries may be formed with anisotropy by varying either one or both of link size and shape, by varying strut size and shape, or by selectively fusing some links to each other. Links may be coated with various biocompatible substances, such as but not limited to hydroxyapatite, to facilitate biological bone ingrowth. Links also may be coated to minimize wear and also with antibiotic eluting coating in order to treat infection.

Figure 21:
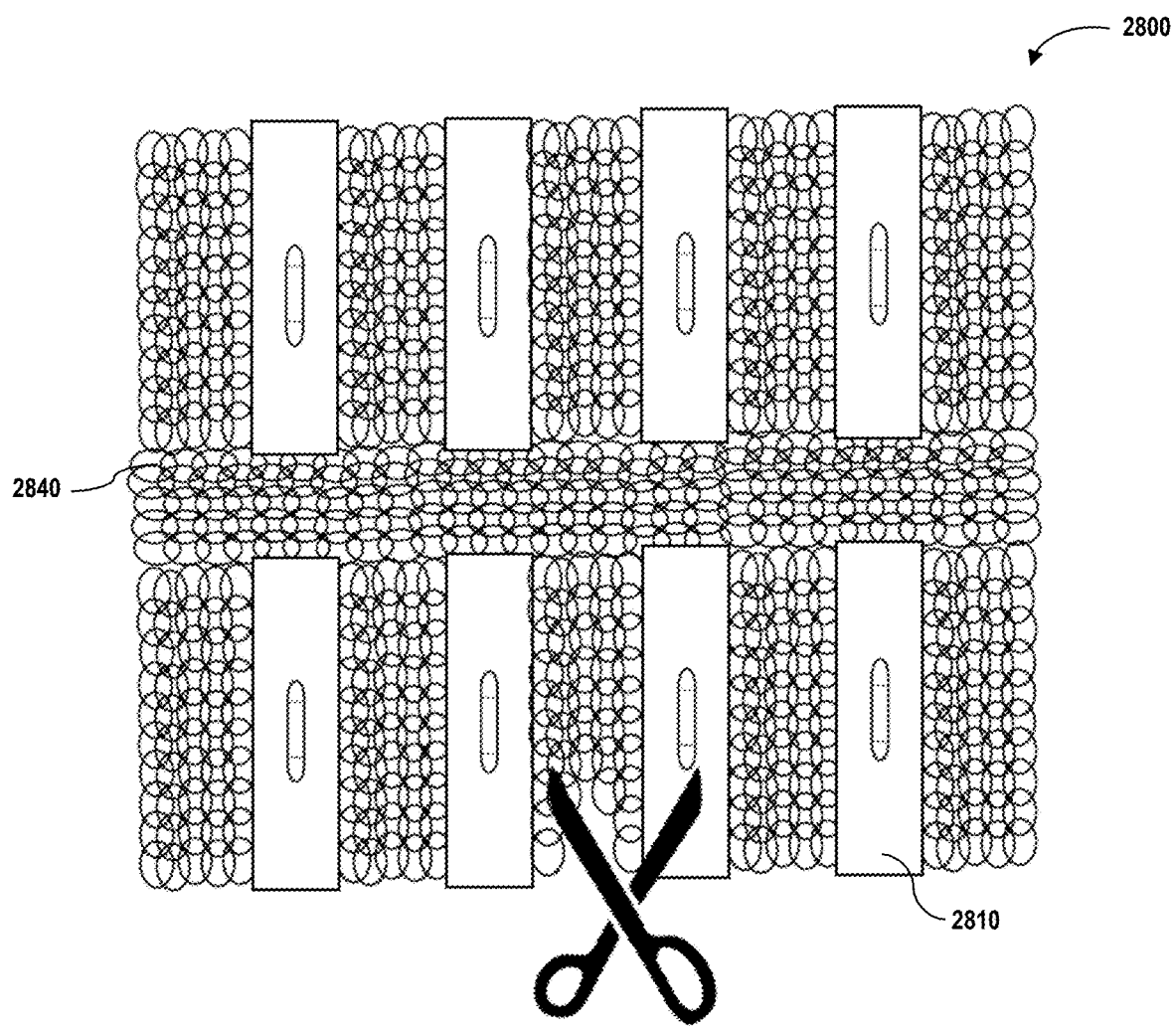
FIG. 21 is a plan view of a bone repair device being trimmed in accordance with an embodiment.

Following formation of a flexible construct such as chain link mesh constructs, mechanical and flexural properties may be adjusted by various post-processing techniques. In one arrangement, the flexible construct may be rolled into a cylinder, increasing the yield strength of the construct along the axis of the cylinder. In another arrangement, one flexible construct may be stacked onto or nested within another flexible construct such that the stacked or nested constructs interact to constrain or augment each other. In some applications, the flexible construct may be shaped, such as by rolling or flattening, such that the construct does not transmit compressive loads. With reference to the example of FIG. 21, large bone repair device 2800 similar in structure to bone repair device 2400 includes a set of plates 2810 interconnected by flexible structure 2840. Flexible structure 2840 may be formed of chain link mesh constructs, which may be trimmed to size by a pair of scissors, producing little debris relative to other devices that require modification from a Midas Rex or similar device.

Figure 22:
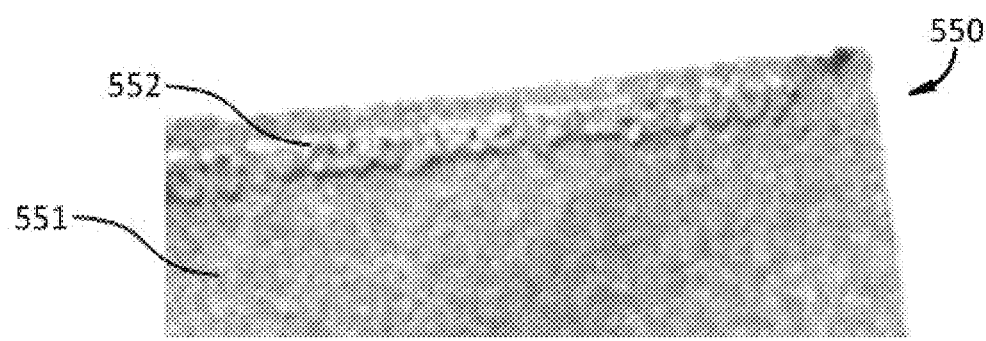
FIGS. 22-23B are views of mesh sheets in accordance with various embodiments.

Referring now to FIGS. 22-27, the chain link and mesh sheets may be produced along with additional features by any one or any combination of the ALM processes described previously herein. As shown in FIG. 22, mesh sheet 550 includes a woven mesh pattern 551 and an alphanumeric pattern 552 fused to the woven mesh pattern, in which the alphanumeric pattern is formed substantially as shown and described in the '010 Patent, using an ALM device. During preparation of mesh sheet 550, successive layers are added to basic mesh pattern 551 to form alphanumeric pattern 552. In this manner, alphanumeric pattern may be used as product identifiers.

Figure 23B:
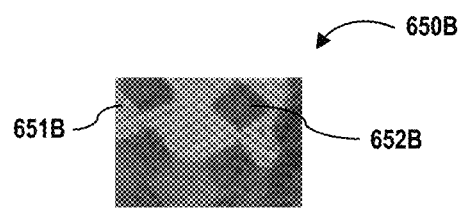

As shown in FIGS. 23A and 23B, mesh sheets may include porous attachment components. In the example of FIG. 12A, mesh sheet 650A includes chain link pattern 651A and a porous attachment component 652A fused to the chain link pattern at spaced-apart regions of the chain link pattern. In the example of FIG. 23B, mesh sheet 650B includes woven mesh pattern 651B and porous attachment component 652B. In these examples, porous attachment components 652A, 652B have been added to both sides of woven mesh pattern 651B during an ALM process. Porous attachment components may be lattice structures such as those disclosed in the '332 Publication as in the example shown, or may be in the form of woven mesh or chain link patterns. In applications for facilitating biological attachment of bone, porous attachment components, such as porous attachment components 652A, 652B, may be used and may have a pore size in the range of approximately 10-1000 µm and a porosity which preferably may be at least 50%. Porous attachment components designed to function as scaffold cells for biological regeneration preferably may have a pore size greater than 100 µm and a porosity greater than 55%. In alternative arrangements (not shown), porous attachment components may be other types of porous structures including but not limited to woven mesh or chain link mesh structures, which may have a pore size and porosity that is different than the mesh, chain link pattern, or other pattern, which may be porous or non-porous, to which the porous attachment components may be attached.

As shown in FIG. 24B, physical eyelet 760 may be integrated into the mesh sheets, such as those that may be used for any of the bone repair devices disclosed previously herein and chain link mesh sheet 750 in this example, during an ALM process. Physical eyelet 760 may be modeled as solid eyelet geometry 760A as shown in FIG. 24A having inner perimeter 761, which may act as a through bore. Depending on the parameter settings of the ALM device, eyelet 760 may be substantially solid or somewhat porous through its thickness, upon production of the physical structure of the eyelet, as shown in FIG. 24B. Mesh sheet 750 was built in its entirety in layers using an ALM process. As shown, some of hexagonal links 755 of mesh sheet 750 abut outer perimeter 762 of eyelet 760. Some of such links 755 have open perimeters in which ends of the open perimeters of the links are fused to eyelet 760. Eyelet 760 may be but is not limited to being used for screw, wire, or cable attachment of mesh sheet 750 to other objects, such as bone or other tissue.

Figure 25A:
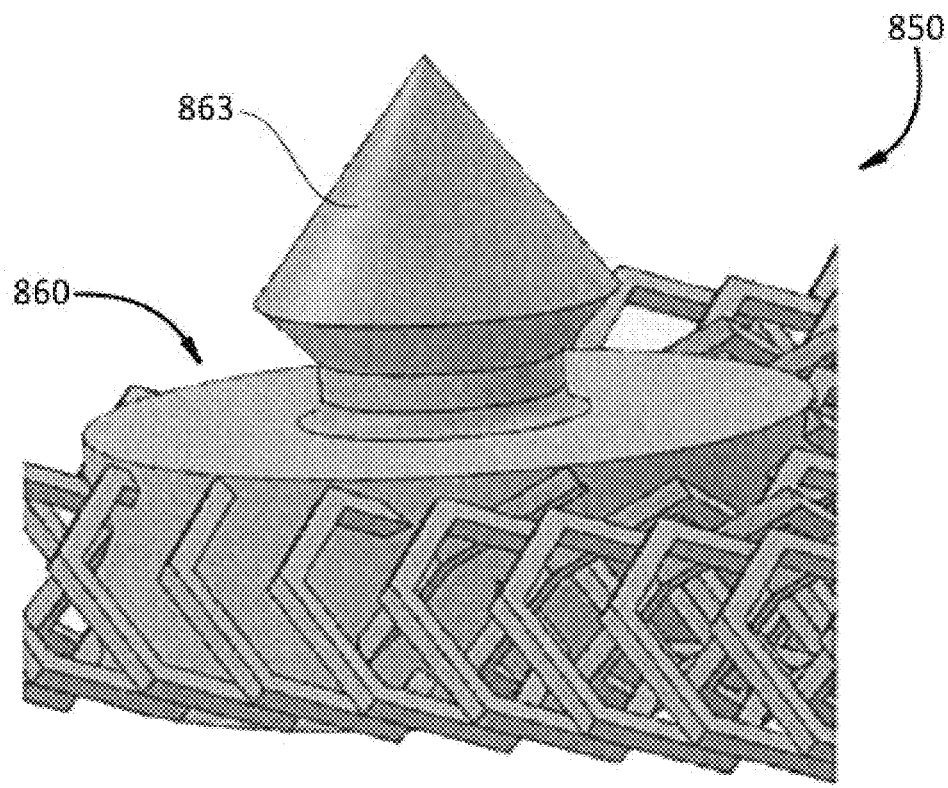
FIGS. 25A-26 are perspective views of three-dimensional model representations of a portion of mesh sheets in accordance with an embodiment.
Figure 25B:
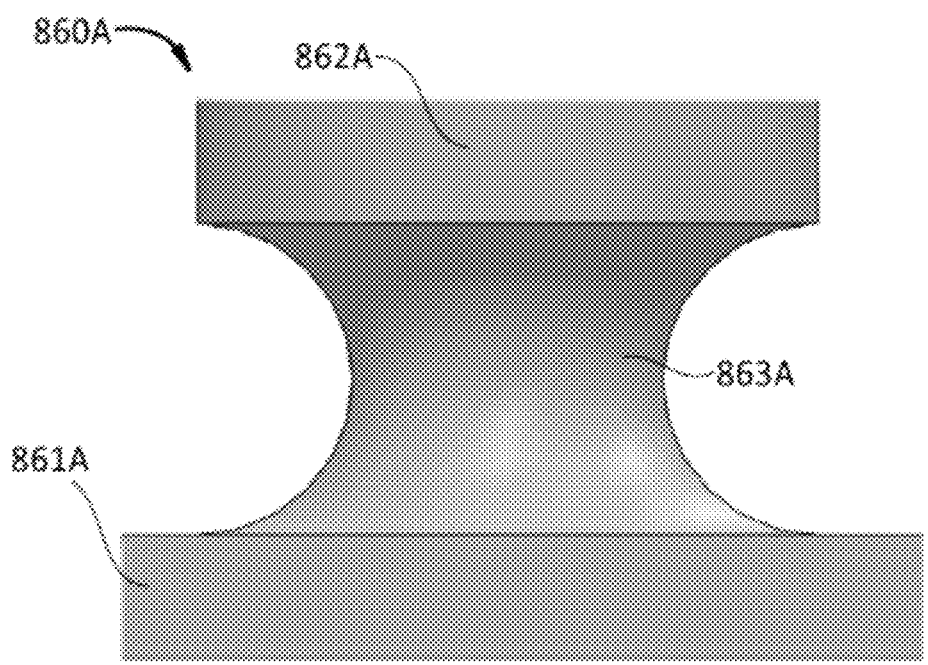

Referring to FIG. 25A, a CAD model includes mesh sheet geometry 850 including stud geometry 860, which as shown may be a rivet, which may be used to prepare a corresponding mesh sheet, such as a mesh sheet used for any of the bone repair devices disclosed previously herein, with a corresponding stud. The stud corresponding to stud geometry 860 may be formed in the same manner as eyelet 760 and thus may be substantially solid or somewhat porous through its thickness and may be fused to links, with the exception that the stud may include a spike, corresponding to spike geometry 863, and may not include any type of through bore. Such studs may allow the construct to be press fit to itself or other materials, including bone. In some alternative arrangements (not shown), a stud geometry may include a through hole.

As shown in FIG. 26B, stud geometry 860A, which may be prepared and used in place of stud geometry 860, includes a lower base geometry 861A, an upper base geometry 862A, and an intermediate section geometry 863A between the lower and upper bases. The stud corresponding to each stud geometry 860A may be fused to the rest of a mesh sheet at a lower base corresponding to lower base geometry 861A, which may be porous, substantially solid, or solid. Studs corresponding to stud geometries 860A may be formed, such as by an ALM process as described previously herein, such that a cable may be wrapped around an intermediate section of a stud corresponding to stud geometry 860A. When placed on or near opposite ends of a bone repair device, such as those disclosed previously herein, such a bone repair device may be tensioned to form a rolled construct, which in some arrangements may be used to enclose other objects, which may be anyone or any combination of bone, another implant such as a femoral stem, and bone graft material.

Figure 26:
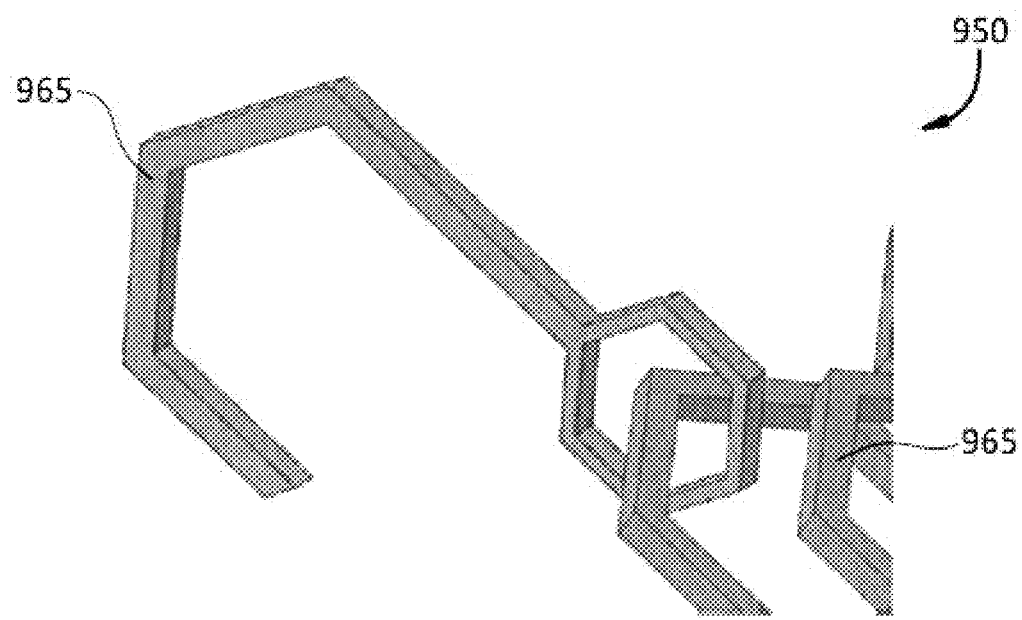

Referring to FIG. 26, a hook may be added to the perimeter of a link as demonstrated by hook geometry 965 attached at a vertex of hexagonal link geometry 955 at an outer perimeter of mesh sheet geometry 950. As shown, hook geometry 965 is in the form of a hexagonal link geometry having an opening at its perimeter. When prepared as a physical structure, the mesh sheet corresponding to mesh sheet geometry 950 may be attached by the hook corresponding to hook geometry 965 to other materials, including but not limited to biological and manufactured materials, or may be attached to another portion of mesh sheet itself to form a wrap or covering.

Figure 27:
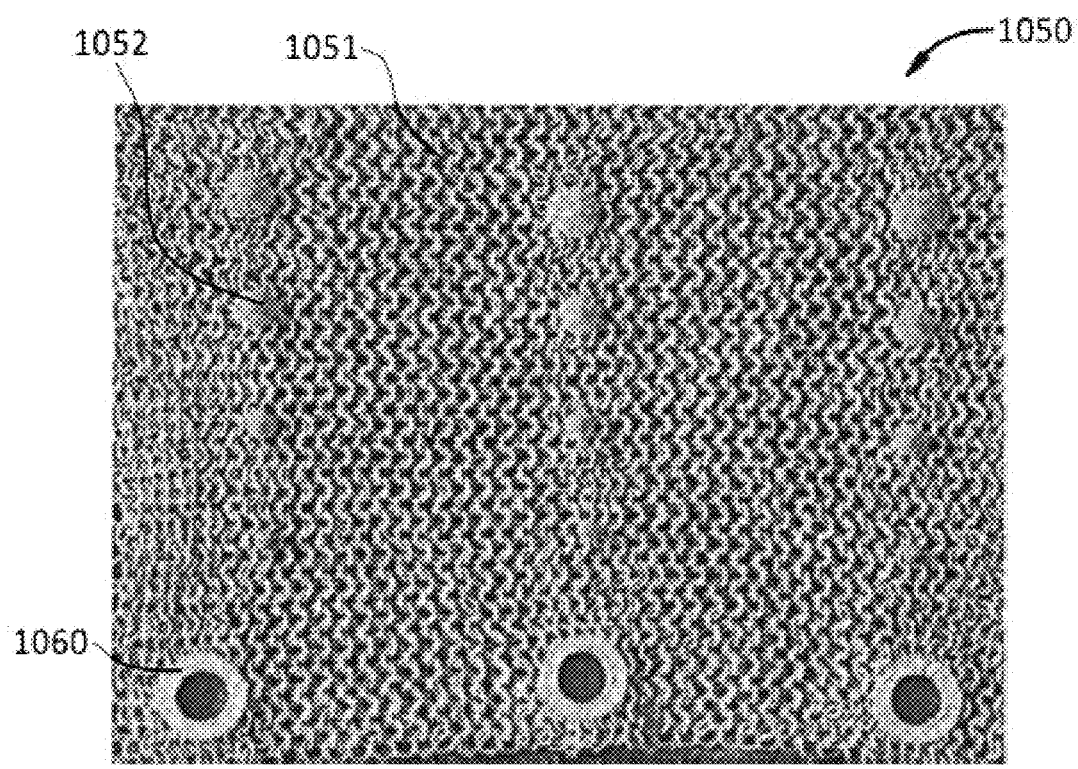
FIG. 27 is an example of a mesh sheet in accordance with an embodiment.

As shown in FIG. 27, mesh sheet 1050 which may be used as a flexible structure for a bone repair device such as any of those described previously herein, includes a plurality of porous attachment components 1052 and eyelets 1060 fused to chain link mesh pattern 1051. Other combinations of features including but not limited to woven mesh patterns, chain link mesh patterns, porous attachment components, and eyelets may be combined into single mesh sheets in accordance with the present technology. In some arrangements, mesh sheet 1050 may be used in applications designed to facilitate biological attachment of soft tissue, including muscles, tendons, and ligaments. In such arrangements, the porous attachment components preferably may have a pore size greater than 100 μm and a porosity greater than 55%.

In some alternative arrangements, flexible structures of any of the bone repair devices described previously herein may have a variable porosity, i.e., variable density, which may be but is not limited to being a graded porosity, by varying any combination of the size and shape of pore cells, i.e., constructed open cells, defined by the struts within the tube device to provide for any one or any combination of variable flexibility, variable range of motion, and variable strength throughout the tube device. In some arrangements, the tube device may be formed with anisotropy in addition to being, or may otherwise be provided with, other unique characteristics by varying any combination of pore cell size and shape, strut size and shape, or by selectively fusing some pore cells to each other.

Figure 28:
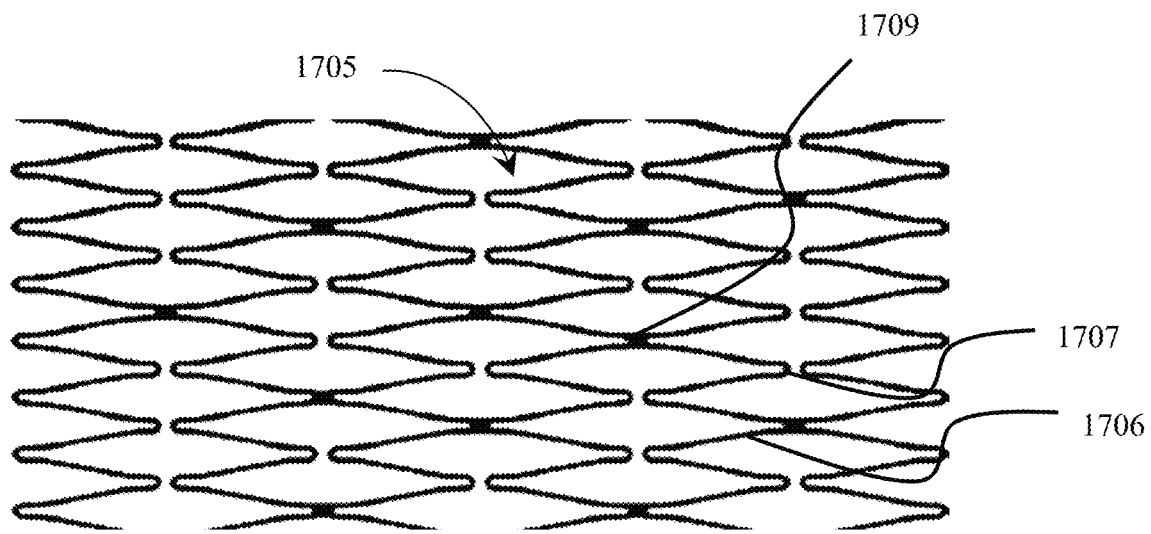
FIGS. 28-30 are perspective views of portions of bone repair devices in accordance with various embodiments.

Referring now to FIG. 28, a flexible structure, such as the flexible structures of any of the bone repair devices disclosed previously herein, may include long segments 1705 having a wavy pattern defined by linear sections 1706 and curved sections 1707. As shown, segments 1705 fuse with adjacent segments at periodic intervals 1709 at adjacent curved sections 1707. In alternative arrangements, adjacent segments may be fused at adjacent curved sections at fewer or greater intervals, including at all instances of adjacency of curved sections of adjacent segments.

Figure 29:
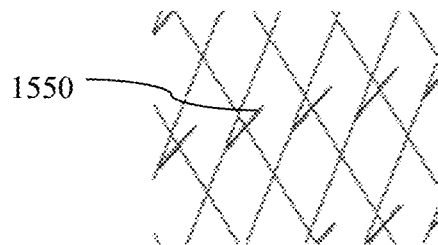

Referring to FIG. 29, projections 1550 may be provided on a flexible structure of a bone repair device, such as any of the bone repair devices disclosed previously herein. Such projections may be configured to interface with host tissue or blood clots in order to break up such clots. Each projection 1550 may extend in any direction from the flexible structure to which it is attached, including outwardly away from the flexible structure, inwardly toward the center of the flexible structure, or within a portion of the flexible structure, such as in a pore cell or a link as described previously herein, to provide an obstruction. In some arrangements, projections on a flexible structure may extend in different directions. Any such projections may be fabricated, such as by any one or any combination of the additive manufacturing processes described previously herein, during the fabrication of the flexible structure of the bone repair device.

Figure 30:
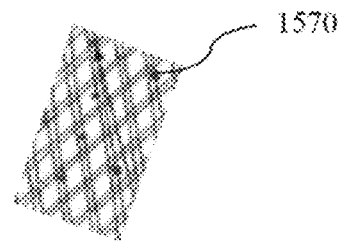

Referring now to FIG. 30, radiopaque markers 1570 that are detectable during imaging, such as through the use of x-rays may be provided on a bone repair device, such as on a porous cell structure as shown or other flexible structure of any of the bone repair devices described previously herein. As in this example, radiopaque markers may be formed by melting deposited metal powder at predetermined locations, such as within or on formed links such as links corresponding to link geometries 455A, 455B, during the fabrication of a bone repair device, such as by process 190 described previously herein. The metal powder to form radiopaque markers 1570 preferably may be platinum which may be blended with other metal powders such as those described previously herein for use in the additive manufacturing process. A predetermined amount of platinum may be used depending on the desired level of radiopacity of the radiopaque markers.

In some arrangements, open links each having adjacent ends defining an opening may be used in place of closed links such as 1545 of flexible structures 1540A-1540C of bone repair device 1500 described previously herein. In some arrangements, the number of links attached to any one link, i.e., the density of links, may be greater or less than the density of links, 8 links attached per link, described previously herein with respect to links 1545. In some arrangements, the density of the links may vary throughout any given flexible structure.

In some arrangements, the plates of the bone repair device may be thinner or thicker than the plates of bone repair devices, such as those of bone repair devices 1500, 1600, 1700, and 2000, described previously herein. In some arrangements, the plates may be either one or both concave on top and convex on bottom. Depending on the application for which a bone repair device is being used, the plates of the bone repair device may be secured to bone parts of a bone requiring repair by threading at least one fastener, e.g., at least one screw, through such holes without the need for any cable.

In some arrangements, the plates having partial loops may have any number of partial loops, and likewise plates having channels may have any number of channels, as the size of such plates permits. Such partial loops may be attached at only one end in contrast to being attached at both ends of the partial loop as in partial loops 1520 of plates 1510A, 1510B. In various arrangements, partial loops may be in any configuration that defines a pathway, such as in a shape having a rectangular or triangular profile.

Channels within plates of a bone repair device having such channels may extend in any direction through the plates as the size of the plates permits. A bone repair device having such channels may have any number of channels as the size of the plates of the bone repair device permits.

In some arrangements, any flexible structures of bone repair devices may have additional layers of links that may be stacked and fused together at various locations to add rigidity to the flexible structure as desired. Any of the other plates described previously herein, including porous plates, plates with loops, and plates with any type of channel extending through the plate may be reconfigured to allow for a continuous flexible structure in a similar manner as plates 1510A, 1510B are reconfigured into separated plates 2410A, 2410B and separated plates 2410C, 2410D, respectively, and as shown in FIGS. 10A-10C, 12B, and 13B.

In some alternative arrangements of any of the bone repair devices described previously herein, the bone repair device may be formed through the creation of CAD models based on patient-specific data obtained through image scans using magnetic resonance imaging (MRI), computed tomography (CT) or microCT, or other known processes.

In some alternative arrangements, any of the bone repair devices described previously herein may be fabricated to have specific surface micro-topologies to create desirable in vivo performance Such micro-topologies that may be controlled preferably include any combination of a variable surface roughness to influence flow dynamics, cell adhesion, and a surface area/volume ratio. Such topologies may be formed by varying fabrication process parameters, such as during an ALM process used to make the devices, or by post-processing techniques such as acid etching which is described in greater detail in the '332 Publication incorporated by reference previously herein, media blasting, heat treatment, electropolishing, thin film deposition, ion bombardment, or other known processes.

It is to be understood that the disclosure set forth herein includes all possible combinations of the particular features set forth above, whether specifically disclosed herein or not. For example, where a particular feature is disclosed in the context of a particular aspect, arrangement, configuration, or embodiment, that feature can also be used, to the extent possible, in combination with and/or in the context of other particular aspects, arrangements, configurations, and embodiments of the invention, and in the invention generally.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A bone repair device comprising:
   a plate including opposing top and bottom surfaces, and a pathway extending across a length of the plate or a width of the plate transverse to the length; and
   a flexible structure including a plurality of overlapping segment geometries, the flexible structure being directly attached to and extending from the plate,
   wherein the plate and an end of the flexible structure are integral with each other such that they are inseparable.

2. The bone repair device of claim 1, wherein the pathway is a channel inset from the top surface of the plate such that the channel forms an exposed surface extending across the respective one of the length or the width of the plate.

3. The bone repair device of claim 1, wherein the pathway is a recess that extends through the plate and intersects a first side of the plate extending between the top and bottom surfaces.

4. The bone repair device of claim 1, wherein the pathway is a channel that extends through the plate and intersects a first side of the plate extending between the top and bottom surfaces, and wherein the channel is open at its ends.

5. The bone repair device of claim 4, wherein the channel is a closed channel covered by the top and the bottom surfaces.

6. The bone repair device of claim 1, wherein the pathway extends at an oblique angle to a first side of the plate extending between the top and bottom surfaces.

7. The bone repair device of claim 1, wherein the plate is a first plate, the bone repair device further comprising a second plate, and wherein the flexible structure is attached to a first side of the first plate extending between the top and bottom surfaces and to a side of the second plate.

8. The bone repair device of claim 1, wherein the flexible structure is in the form of chain mail defined by the plurality of overlapping segment geometries.

9. The bone repair device of claim 1, wherein at least the bottom surface of the plate is continuously curved.

10. The bone repair device of claim 1, wherein a cross-section of the plate taken within a plane across the length or the width of the plate is curved.

11. The bone repair device of claim 1, further comprising a porous structure extending from the bottom surface of the plate.

12. The bone repair device of claim 1, wherein the pathway extends across an entire length of the plate or an entire width of the plate transverse to the length, the pathway further extending through at least one outer side surface intersecting the top and the bottom surfaces.

13. A bone repair device comprising:
   a plate including a pathway extending across a length of the plate or a width of the plate transverse to the length; and
   a flexible structure directly attached to the plate, wherein the pathway includes a loop and linear portions extending from the loop, and wherein at least one of the linear portions intersects a surface of the plate.

14. The bone repair device of claim 13,
   wherein the plate further includes top and bottom surfaces and a first side extending between the top and the bottom surfaces,
   wherein the plate further includes a second side extending between the top and the bottom surfaces and opposite the first side of the plate, and wherein one of the linear portions intersects the first side of the plate defining the surface and another one of the linear portions intersects the second side of the plate.

15. A surgical method comprising the steps of:
placing a bone repair device including a plate and a flexible structure around and over a plurality of bone parts, the plate including opposing top and bottom surfaces, wherein the flexible structure includes a plurality of overlapping segment geometries directly attached to and extending from the plate; and
securing the plate to the plurality of bone parts with a cable inserted along a pathway defined by the plate of the bone repair device and wrapped around the bone parts.

16. The method of claim 15, further comprising a step of inserting the cable through the pathway defined by the plate of the bone repair device.

17. The method of claim 16, wherein the inserting step includes inserting the cable through an opening in the top surface.

18. The method of claim 16, wherein the cable is inserted at an oblique angle to a first side of the plate extending between the top and bottom surfaces.

19. The method of claim 15, further comprising a step of wrapping the cable around the bone parts.

20. The method of claim 15, wherein the cable is a cerclage wire.

* * * * *